US010822395B2

(12) United States Patent
Loukas et al.

(10) Patent No.: US 10,822,395 B2
(45) Date of Patent: Nov. 3, 2020

(54) MODIFIED ANTI-INFLAMMATORY PROTEINS AND METHOD OF USE

(71) Applicant: James Cook University, Townsville (AU)

(72) Inventors: Alex Loukas, Townsville (AU); Andrew Leech, Townsville (AU); Darren Pickering, Townsville (AU)

( * ) Notice: Subject to any disclaimer, the term of this patent is extended or adjusted under 35 U.S.C. 154(b) by 0 days.

(21) Appl. No.: 15/023,165

(22) PCT Filed: Sep. 18, 2014

(86) PCT No.: PCT/AU2014/050240
§ 371 (c)(1),
(2) Date: Mar. 18, 2016

(87) PCT Pub. No.: WO2015/039189
PCT Pub. Date: Mar. 26, 2015

(65) Prior Publication Data
US 2016/0229905 A1    Aug. 11, 2016

(30) Foreign Application Priority Data

Sep. 18, 2013 (AU) ............................... 2013903588

(51) Int. Cl.
| A61K 38/00 | (2006.01) |
| A61P 29/00 | (2006.01) |
| A61K 38/16 | (2006.01) |
| A61P 11/06 | (2006.01) |
| C07K 14/81 | (2006.01) |
| A61K 45/06 | (2006.01) |
| C07K 14/435 | (2006.01) |
| A61K 38/57 | (2006.01) |

(52) U.S. Cl.
CPC .............. *C07K 14/81* (2013.01); *A61K 38/57* (2013.01); *A61K 45/06* (2013.01); *C07K 14/4354* (2013.01); *C07K 14/8146* (2013.01); *A61K 38/00* (2013.01)

(58) Field of Classification Search
None
See application file for complete search history.

(56) References Cited

U.S. PATENT DOCUMENTS

| 7,842,788 B2 | 11/2010 | Silbiger et al. |
| 2003/0143693 A1 | 7/2003 | Silbiger et al. |
| 2003/0195143 A1 | 10/2003 | Kramer et al. |
| 2004/0235724 A1 | 11/2004 | Berdel et al. |
| 2005/0042232 A1 | 2/2005 | Hotez et al. |
| 2005/0070477 A1 | 3/2005 | Cochrane |
| 2014/0274874 A1 | 9/2014 | Ketchem et al. |
| 2015/0037366 A1* | 2/2015 | Loukas ................. A61K 38/57 424/191.1 |

FOREIGN PATENT DOCUMENTS

| CA | 2430973 A1 | 6/2002 |
| JP | 2000-007575 A | 1/2000 |
| WO | WO-1993/023063 | 11/1993 |
| WO | WO-2006/019962 | 2/2006 |
| WO | WO-2007/005672 | 1/2007 |
| WO | WO-2007/016482 | 2/2007 |
| WO | WO-2010/048432 | 4/2010 |
| WO | WO-2011/119484 | 9/2011 |
| WO | WO-2013/134822 | 9/2013 |
| WO | WO-2013134822 A1 * | 9/2013 ............ A61K 38/57 |

OTHER PUBLICATIONS

Zhan et al. "Molecular cloning and characterization of Ac-TMP-2, a tissue inhibitor of metalloproteinase secreted by adult Ancylosotoma caninum" Molecular and Biochemical Parasitology 162:142-148. Published Aug. 30, 2008.*
Cazzola et al. "Emerging anti-inflammatory strategies for COPD" European Respiratory Journal 40:724-741. Published Apr. 10, 2012.*
Tremaine WJ "Refractory IBD: medical management" Netherlands Journal of Medicine 50:S12-S14. Published Feb. 1997.*
Caterina et al. "Glycosylation and NH2-terminal domain mutant of the tissue inhibitor of metalloproteinases-1 (TIMP-1)" Biochimica et Biophysica Acta 1398:21-34. (Year: 1998).*
An et al. "Determination of Glycosylation Sites and Site-Specific Heterogeneity in Glycoproteins" Current Opinion in Chemical Biology 13:421-426. (Year: 2009).*
Cuellar, C. et al., The Hookworm Tissue Inhibitor of Metalloproteases (Ac-TMP-1) Modifies Dendritic Cell Function and Induces Generation of CD4 and CD8 Suppressor T Cells, *PLOS Neglected Tropical Diseases*, 3(5): 1-9, e439, 2009.
REFSEQ Accession No. NP_001087748, Apr. 17, 2013.
Ferreira, I. et al., Hookworm Excretory/Secretory Products Induce Interleukin-4 (Il-4)+ IL-10+ CD4+ T Cell Responses and Suppress Pathology in a Mouse Model of Colitis, Infection and Immunity, 81(6): 2104-2111, Jun. 2013.
Ruyssers, N. et al., Therapeutic Potential of Helminth Soluble Proteins in TNBS-induced Colitis in Mice, *Inflamm Bowel Dis*, 15(4): 491-500, Apr. 2009.

(Continued)

*Primary Examiner* — Larry D Riggs, II
*Assistant Examiner* — Zachary J Miknis
(74) *Attorney, Agent, or Firm* — Julie K. Staple; Dinsmore & Shohl LLP

(57) ABSTRACT

A modified Ac-TMP-2 protein lacks one or a plurality of acidic C-terminal amino acids normally present in a full-length or wild-type Ac-TMP-2 protein and may also lack one or a plurality of N-terminal amino acids while retaining the amino acid sequence C—S—C at or near the N-terminus. The modified Ac-TMP-2 protein may be useful in method and composition for reducing or alleviating inflammation in a subject. Inflammation may be associated with a disease is a disease of the digestive tract such as chronic gastritis or an inflammatory bowel disease such as Crohn's disease or ulcerative colitis, or a disease of the respiratory system, such as asthma, emphysema, chronic bronchitis, and chronic obstructive pulmonary disease.

11 Claims, 11 Drawing Sheets
Specification includes a Sequence Listing.

(56) References Cited

OTHER PUBLICATIONS

Zhan, B. et al., Molecular cloning and characterization of Ac-TMP-2, a tissue inhibitor of metalloproteinase secreted by adult Ancylostoma caninum, *Molecular & Biochemical Parasitology*, 162: 142-148, 2008.

Butler et al., The Specificity of TIMP-2 for Matrix Metalloproteinases Can Be Modified by Single Amino Acid Mutations, *Biol. Chem.*, 274 (29): 20391-20396, 1999.

Mulvenna et al., Proteomics Analysis of the Excretory/Secretory Component of the Blood-feeding stage of the Hookworm, Ancylostoma caninum, *Mol Cell. Proteomics*, 8.1: 109-121, 2009.

International Search Report (ISR) for PCT/AU2013/000247, dated Apr. 23, 2013.

International Preliminary Report on Patentability (IPRP) for PCT/AU2013/000247 with amended sheets, dated Sep. 26, 2013.

Kucera, K. et al., Ancylostoma ceylanicum Excretory-Secretory Protein 2 Adopts a Netrin-Like Fold and Defines a Novel Family of Nematode Proteins, *Journal of Molecular Biology*, 408: 9-17, 2011.

EP Appl. No. 14845336.8 Supplemental European Search Report, Mar. 6, 2017.

Croese, J., A proof of concept study establishing Necator americanus in Crohn's patients and reservoir donors, GUT, 55(1): 136-137. Jan. 1, 2006.

Falcone, F. et al., Parasite role reversal: worms on trial, *Trends in Parasitology*, 21(4): 157-160, Apr. 1, 2005.

Cantacessi, C. et al., TIMPS of parasitic helminths—a large-scale analysis of high-throughput sequence datasets, *Parasites & Vectors*, 6: 156, 2013.

Nath, M. et al., New triorganotin(IV) derivatives of dipeptides as anti-inflammatory-antimicrobial agents: European *Journal of Medicinal Chemistry*, 40: 289-298, 2005.

Pearson, Molecular mechanisms of hookworm disease: Stealth, virulence, and vaccines, J Allergy Clin Immunol, 130:13-21, Jul. 2012.

Wilson, R., Bacteria, antibiotics and COPD, *Eur Respir J*, 17:995-1007, 2001.

Heuschkel, R. et al., Imbalance of stromelysin-1 and TIMP-1 in the mucosal lesions of children with inflammatory bowel disease, Gut, 47:57-62, 2000.

Ajmone-Cat, M. et al., Non-steroidal Anti-Inflammatory Drugs and Brain Inflammation: Effects on Microglial Functions, *Pharmaceuticals*, 3:1949-1964, 2010.

Kumagai, K. et al., The involvement of matrix metalloproteinases in basement membrane injury in a murine model of acute allergic airway inflammation, Clin Exp Allergy., 32(10):1527-34, Oct. 2002.

Miyoshi, H. et al.,, Beneficial effects of tissue inhibitor of metalloproteinases-2 (TIMP-2) on chronic dermatitis, J Dermatol., 32(5):346-53, May 2005.

Van Assche, G., Emerging drugs to treat Crohn's disease, Expert Opin Emerg Drugs, 12(1):49-59, Mar. 2007.

\* cited by examiner

N-Term Ac-TIMP-2 coding and amino acid sequence.

```
gaggctgaagctgaattcgcatgctcttgcaaaccgttcggaacactgaaggaagctttc
 E   A   E   A   E   F   A   C   S   C   K   P   F   G   T   L   K   E   A   F
tgccaatcagattacgtgcttctggcaaaagtgttgtcagtaaatagtaaatatggtgaa
 C   Q   S   D   Y   V   L   L   A   K   V   L   S   V   N   S   K   Y   G   E
tcgtcgagaaatgaagcaaatgatatgagcacgaccgctaacggaacatggagttaccat
 S   S   R   N   E   A   N   D   M   S   T   T   A   N   G   T   W   S   Y   H
gtatggcacatgcggacttggaagggtcctgtcgttgatactagtgttctcaccacgtca
 V   W   H   M   R   T   W   K   G   P   V   V   D   T   S   V   L   T   T   S
tatagcgagtgtggtgtaactggtctcttgaaaaattgggattattttctaacaggcaag
 Y   S   E   C   G   V   T   G   L   L   K   N   W   D   Y   F   L   T   G   K
caaggaaaagatggcgaaatcaccatcacaagctgcgactttgtaatgccatcaactgat
 Q   G   K   D   G   E   I   T   I   T   S   C   D   F   V   M   P   S   T   D
gtcacaccagaagagcatgatcttttgatggacctcatggggacccgaaaaaatgtgaa
 V   T   P   E   E   H   D   L   L   M   D   L   M   G   D   P   K   K   C   E
gaaaaagatgatgagagggacggtctagaacaaaaactcatctcagaagaggatctgaat
 E   K   D   D   E   R   D   G   L   E   Q   K   L   I   S   E   E   D   L   N
agcgccgtcgaccatcatcatcatcatcattga
 S   A   V   D   H   H   H   H   H   H   -
```

```
ACSCKPFGTLKEAFCQSDYVLLAKVLSVNSKYGESSRNEANDMSTTANGTWSYHVWHMRTWKGPVVDTS
VLTTSYSECGVTGLLKNWDYFLTGKQGKDGEITITSCDFVMPSTDVTPEEHDLLMDLMGDPKKCEEKDD
ERD (SEQ ID NO:1)
```

**GAGGCTGAAGCTGAATTCGCATGCTCTTGCAAACCGTTCGGAACACTGA
AGGAAGCTTTCTGCCAATCAGATTACGTGCTTCTGGCAAAAGTGTTGTCA
GTAAATAGTAAATATGGTGAATCGTCGAGAAATGAAGCAAATGATATGAG
CACGACCGCTAACGGAACATGGAGTTACCATGTATGGCACATGCGGACTT
GGAAGGGTCCTGTCGTTGATACTAGTGTTCTCACCACGTCATATAGCGAGT
GTGGTGTAACTGGTCTCTTGAAAAATTGGGATTATTTTCTAACAGGCAAGC
AAGGAAAAGATGGCGAAATCACCATCACAAGCTGCGACTTTGTAATGCCA
TCAACTGATGTCACACCAGAAGAGCATGATCTTTTGATGGACCTCATGGG
GGACCCGAAAAAATGTGAAGAAAAAGATGATGAGAGGGACGGTCTAGAA
CAAAAACTCATCTCAGAAGAGGATCTGAATAGCGCCGTCGACCATCA
TCATCATCATTGA**

FIG. 1

Bold is vector sequence
<u>Double underlined</u> is Restriction site derived sequence
<u>Single underlined</u> is the amino acid sequence of Ac-AIP-2
N-Q is the single amino acid mutation. N is the wild type sequence, Q is the mutated sequence.

Ac-AIP-2 $_{WT}$ (Mature wild type full length sequence)
EAEA<u>EFACSCKPFGTLKEAFCQSDYVLLAKVLSVNSKYGESSRNEANDMSTT
ANGTWSYHVWHMRTWKGPVVDTSVLTTSYSECGVTGLLKNWDYFLTGKQ
GKDGEITITSCDFVMPSTDVTPEEHDLLMDLMGDPKKCEEKDDERDVKENEN
SVEENDEKDEEENGEKTVEENDEKTVEENDEKVEEENGEKTVEENDEKIVEE
NDEKDEEENGEKTVEENDEKTVEENDEQEGL</u>**EQKLISEEDLNSAVDHHHH
HH**

Ac-AIP-2$_{Q48}$ (Mature N-glycan mutant full length sequence)
EAEA<u>EFACSCKPFGTLKEAFCQSDYVLLAKVLSVNSKYGESSRNEANDMSTT
AQGTWSYHVWHMRTWKGPVVDTSVLTTSYSECGVTGLLKNWDYFLTGKQ
GKDGEITITSCDFVMPSTDVTPEEHDLLMDLMGDPKKCEEKDDERDVKENEN
SVEENDEKDEEENGEKTVEENDEKTVEENDEKVEEENGEKTVEENDEKIVEE
NDEKDEEENGEKTVEENDEKTVEENDEQEGL</u>**EQKLISEEDLNSAVDHHHH
HH**

Ac-AIP-2 $_{NT}$ (Mature wild type Netrin domain sequence)
EAEA<u>EFACSCKPFGTLKEAFCQSDYVLLAKVLSVNSKYGESSRNEANDMSTT
ANGTWSYHVWHMRTWKGPVVDTSVLTTSYSECGVTGLLKNWDYFLTGKQ
GKDGEITITSCDFVMPSTDVTPEEHDLLMDLMGDPKKCEEKDDERDGL</u>**EQKL
ISEEDLNSAVDHHHHHH**

Ac-AIP-2$_{NTQ48}$ (Mature N-Glycan Netrin domain sequence)
EAEA<u>EFACSCKPFGTLKEAFCQSDYVLLAKVLSVNSKYGESSRNEANDMSTT
AQGTWSYHVWHMRTWKGPVVDTSVLTTSYSECGVTGLLKNWDYFLTGKQ
GKDGEITITSCDFVMPSTDVTPEEHDLLMDLMGDPKKCEEKDDERDGL</u>**EQKL
ISEEDLNSAVDHHHHHH**

FIG. 2

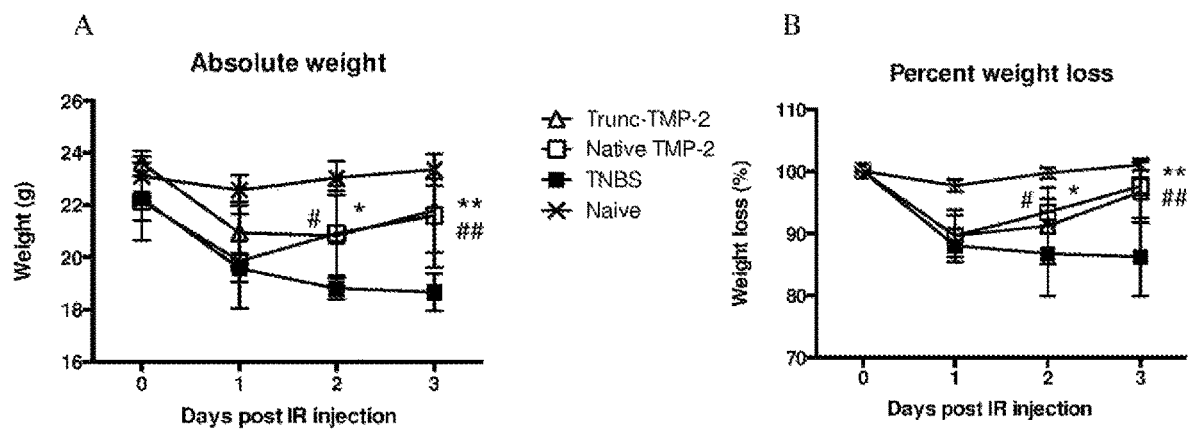
FIG. 3
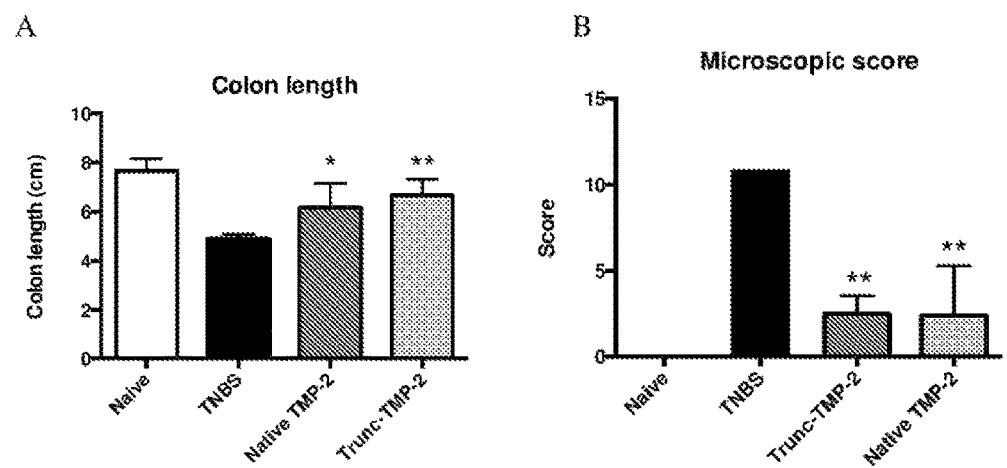
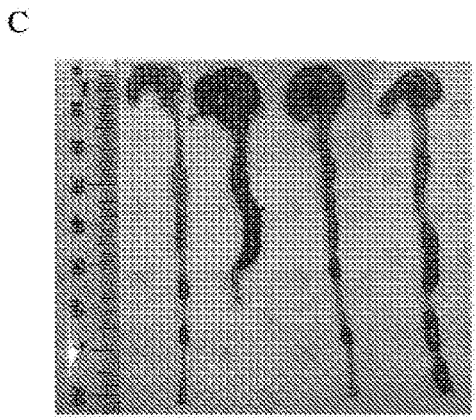
FIG. 4

SEQUENCE LISTING

<160> NUMBER OF SEQ ID NOS: 5

<210> SEQ ID NO 1
<211> LENGTH: 141
<212> TYPE: PRT
<213> ORGANISM: Ancylostoma caninum

<400> SEQUENCE: 1

Ala Cys Ser Cys Lys Pro Phe Gly Thr Leu Lys Glu Ala Phe Cys Gln
1               5                   10                  15

Ser Asp Tyr Val Leu Leu Ala Lys Val Leu Ser Val Asn Ser Lys Tyr
            20                  25                  30

Gly Glu Ser Ser Arg Asn Glu Ala Asn Asp Met Ser Thr Thr Ala Asn

```
            35                  40                  45
Gly Thr Trp Ser Tyr His Val Trp His Met Arg Thr Trp Lys Gly Pro
 50                  55                  60
Val Val Asp Thr Ser Val Leu Thr Thr Ser Tyr Ser Glu Cys Gly Val
 65                  70                  75                  80
Thr Gly Leu Leu Lys Asn Trp Asp Tyr Phe Leu Thr Gly Lys Gln Gly
                     85                  90                  95
Lys Asp Gly Glu Ile Thr Ile Thr Ser Cys Asp Phe Val Met Pro Ser
                100                 105                 110
Thr Asp Val Thr Pro Glu Glu His Asp Leu Leu Met Asp Leu Met Gly
                115                 120                 125
Asp Pro Lys Lys Cys Glu Glu Lys Asp Asp Glu Arg Asp
130                 135                 140

<210> SEQ ID NO 2
<211> LENGTH: 228
<212> TYPE: PRT
<213> ORGANISM: Ancylostoma caninum

<400> SEQUENCE: 2

Ala Cys Ser Cys Lys Pro Phe Gly Thr Leu Lys Glu Ala Phe Cys Gln
 1               5                  10                  15
Ser Asp Tyr Val Leu Leu Ala Lys Val Leu Ser Val Asn Ser Lys Tyr
                 20                  25                  30
Gly Glu Ser Ser Arg Asn Glu Ala Asn Asp Met Ser Thr Thr Ala Asn
                 35                  40                  45
Gly Thr Trp Ser Tyr His Val Trp His Met Arg Thr Trp Lys Gly Pro
 50                  55                  60
Val Val Asp Thr Ser Val Leu Thr Thr Ser Tyr Ser Glu Cys Gly Val
 65                  70                  75                  80
Thr Gly Leu Leu Lys Asn Trp Asp Tyr Phe Leu Thr Gly Lys Gln Gly
                     85                  90                  95
Lys Asp Gly Glu Ile Thr Ile Thr Ser Cys Asp Phe Val Met Pro Ser
                100                 105                 110
Thr Asp Val Thr Pro Glu Glu His Asp Leu Leu Met Asp Leu Met Gly
                115                 120                 125
Asp Pro Lys Lys Cys Glu Glu Lys Asp Asp Glu Arg Asp Val Lys Glu
130                 135                 140
Asn Glu Asn Ser Val Glu Glu Asn Asp Glu Lys Asp Glu Glu Asn
145                 150                 155                 160
Gly Glu Lys Thr Val Glu Glu Asn Asp Glu Lys Thr Val Glu Glu Asn
                165                 170                 175
Asp Glu Lys Val Glu Glu Asn Gly Glu Lys Thr Val Glu Glu Asn
                180                 185                 190
Asp Glu Lys Ile Val Glu Glu Asn Asp Glu Lys Asp Glu Glu Asn
                195                 200                 205
Gly Glu Lys Thr Val Glu Glu Asn Asp Glu Lys Thr Val Glu Glu Asn
                210                 215                 220
Asp Glu Gln Glu
225

<210> SEQ ID NO 3
<211> LENGTH: 423
<212> TYPE: DNA
<213> ORGANISM: Ancylostoma caninum
```

<400> SEQUENCE: 3

```
gcatgctctt gcaaaccgtt cggaacactg aaggaagctt tctgccaatc agattacgtg      60
cttctggcaa aagtgttgtc agtaaatagt aaatatggtg aatcgtcgag aaatgaagca     120
aatgatatga gcacgaccgc taacggaaca tggagttacc atgtatggca catgcggact     180
tggaagggtc ctgtcgttga tactagtgtt ctcaccacgt catatagcga gtgtggtgta     240
actggtctct tgaaaaattg ggattatttt ctaacaggca agcaaggaaa agatggcgaa     300
atcaccatca caagctgcga ctttgtaatg ccatcaactg atgtcacacc agaagagcat     360
gatcttttga tggacctcat gggggacccg aaaaaatgtg aagaaaaaga tgatgagagg     420
gac                                                                    423
```

<210> SEQ ID NO 4
<211> LENGTH: 228
<212> TYPE: PRT
<213> ORGANISM: Ancylostoma caninum

<400> SEQUENCE: 4

```
Ala Cys Ser Cys Lys Pro Phe Gly Thr Leu Lys Glu Ala Phe Cys Gln
1               5                   10                  15

Ser Asp Tyr Val Leu Leu Ala Lys Val Leu Ser Val Asn Ser Lys Tyr
            20                  25                  30

Gly Glu Ser Ser Arg Asn Glu Ala Asn Asp Met Ser Thr Thr Ala Gln
        35                  40                  45

Gly Thr Trp Ser Tyr His Val Trp His Met Arg Thr Trp Lys Gly Pro
    50                  55                  60

Val Val Asp Thr Ser Val Leu Thr Thr Ser Tyr Ser Glu Cys Gly Val
65                  70                  75                  80

Thr Gly Leu Leu Lys Asn Trp Asp Tyr Phe Leu Thr Gly Lys Gln Gly
                85                  90                  95

Lys Asp Gly Glu Ile Thr Ile Thr Ser Cys Asp Phe Val Met Pro Ser
            100                 105                 110

Thr Asp Val Thr Pro Glu Glu His Asp Leu Leu Met Asp Leu Met Gly
        115                 120                 125

Asp Pro Lys Lys Cys Glu Glu Lys Asp Asp Glu Arg Asp Val Lys Glu
    130                 135                 140

Asn Glu Asn Ser Val Glu Glu Asn Asp Glu Lys Asp Glu Glu Asn
145                 150                 155                 160

Gly Glu Lys Thr Val Glu Glu Asn Asp Glu Lys Thr Val Glu Glu Asn
                165                 170                 175

Asp Glu Lys Val Glu Glu Asn Gly Glu Lys Thr Val Glu Glu Asn
            180                 185                 190

Asp Glu Lys Ile Val Glu Glu Asn Asp Glu Lys Asp Glu Glu Asn
        195                 200                 205

Gly Glu Lys Thr Val Glu Glu Asn Asp Glu Lys Thr Val Glu Glu Asn
    210                 215                 220

Asp Glu Gln Glu
225
```

<210> SEQ ID NO 5
<211> LENGTH: 141
<212> TYPE: PRT
<213> ORGANISM: Ancylostoma caninum

<400> SEQUENCE: 5

-continued

```
Ala Cys Ser Cys Lys Pro Phe Gly Thr Leu Lys Glu Ala Phe Cys Gln
1               5                   10                  15

Ser Asp Tyr Val Leu Leu Ala Lys Val Leu Ser Val Asn Ser Lys Tyr
            20                  25                  30

Gly Glu Ser Ser Arg Asn Glu Ala Asn Asp Met Ser Thr Thr Ala Gln
        35                  40                  45

Gly Thr Trp Ser Tyr His Val Trp His Met Arg Thr Trp Lys Gly Pro
    50                  55                  60

Val Val Asp Thr Ser Val Leu Thr Thr Ser Tyr Ser Glu Cys Gly Val
65                  70                  75                  80

Thr Gly Leu Leu Lys Asn Trp Asp Tyr Phe Leu Thr Gly Lys Gln Gly
                85                  90                  95

Lys Asp Gly Glu Ile Thr Ile Thr Ser Cys Asp Phe Val Met Pro Ser
            100                 105                 110

Thr Asp Val Thr Pro Glu Glu His Asp Leu Leu Met Asp Leu Met Gly
        115                 120                 125

Asp Pro Lys Lys Cys Glu Glu Lys Asp Asp Glu Arg Asp
    130                 135                 140
```

MODIFIED ANTI-INFLAMMATORY PROTEINS AND METHOD OF USE

FIELD OF THE INVENTION

THIS INVENTION relates to modified anti-inflammatory proteins and their use for treating inflammation. More particularly, this invention relates to the use of modified hookworm proteins for reducing, alleviating and/or preventing inflammation.

BACKGROUND TO THE INVENTION

Inflammation is a non-specific reaction mounted by the immune system in response to a perceived injury or threat. It is an innate defensive response, distinguished from the more precisely tailored adaptive responses of the immune system. Inflammation may work cooperatively with adaptive responses of the immune system, which develop more slowly but are more precisely targeted to a harmful agent such as a pathogen that may be causing localised injury.

While associated with infection, inflammation occurs in response to many types of injury, including physical trauma, burns (e.g., from radiation, heat or corrosive materials), chemical or particulate irritants, bacterial or viral pathogens, and localized oxygen deprivation (ischemia). Inflammation is also associated with autoimmune diseases and allergic reactions. Inflammation includes the classic symptoms of redness, heat, swelling, and pain, and may be accompanied by decreased function of the inflamed organ or tissue.

While a number of methods for treating inflammation are known, all of them have limitations, particularly with regard to broad based efficacy. Thus, there is a need for new methods for reducing, alleviating and/or preventing inflammation associated with a variety of causes.

SUMMARY OF THE INVENTION

The present invention is directed to methods and compositions for treating and/or preventing inflammation and/or diseases or conditions associated with inflammation.

In a broad form, the invention relates to use of one or more modified proteins, which protein is derivable or obtainable from hookworms including but not limited to *Ancylostoma caninum*, for reducing, alleviating and/or preventing inflammation and/or diseases or conditions associated with inflammation such as asthma and/or inflammatory bowel disease, In one aspect, the invention provides a modified Ac-TMP-2 protein which lacks one or more N-terminal and/or C-terminal amino acids normally present in a full-length or wild-type Ac-TMP-2 protein.

Suitably, the modified Ac-TMP-2 protein has the amino acid sequence C—X—C at or near the N-terminus.

Suitably, the modified Ac-TMP-2 protein is capable of preventing, reducing and/or alleviating inflammation upon administration to a subject.

In one embodiment, the modified Ac-TMP-2 protein comprises an amino acid sequence set forth in SEQ ID NO:1, or an amino acid sequences at least 70% identical thereto.

In one embodiment, the modified Ac-TMP-2 protein comprises an amino acid sequence set forth in SEQ ID NO:2, or an amino acid sequence at least 70% identical thereto.

In one embodiment, the modified Ac-TMP-2 protein comprises an amino acid sequence set forth in SEQ ID NO:4, or an amino acid sequence at least 70% identical thereto.

In one embodiment, the modified Ac-TMP-2 protein comprises an amino acid sequence set forth in SEQ ID NO:5, or an amino acid sequence at least 70% identical thereto.

This aspect also provides fragments, variants and derivatives of the modified Ac-TMP-2 protein.

In another aspect, the invention provides a method of reducing or alleviating inflammation in a subject, the method including the step of administering to the subject a therapeutically effective amount of the modified Ac-TMP-2 protein of the first-mentioned aspect (inclusive of fragments, variants and derivatives thereof), to thereby reduce or alleviate the inflammation.

In one embodiment, this aspect further includes the step of administering to the subject at least one additional agent.

Suitably, according to the above embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In some embodiments, the inflammation is associated with or secondary to a disease, disorder and/or condition in the subject, particularly an immunological disease, disorder and/or condition.

In certain embodiments the disease is a disease of the digestive tract or the respiratory system.

In another embodiment, the disease, disorder and/or condition is refractory to a baseline therapy.

Suitably, according to the above embodiment, the baseline therapy comprises administration of at least one baseline agent selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In yet another aspect, the invention provides a method of preventing inflammation in a subject, the method including the step of administering to the subject a therapeutically effective amount of the modified Ac-TMP-2 protein of the first-mentioned aspect (inclusive of fragments, variants and derivatives thereof), to thereby prevent the inflammation.

In one embodiment, this aspect further includes the step of administering to the subject at least one additional agent.

Suitably, according to this embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In still yet another aspect, the invention provides a method for preventing and/or treating an inflammatory bowel disease in a subject, the method including the step of administering to the subject a therapeutically effective amount of the modified Ac-TMP-2 protein of the first-mentioned aspect (inclusive of fragments, variants and derivatives thereof), to thereby prevent and/or treat the inflammatory bowel disease.

In one embodiment, this aspect further includes the step of administering to the subject at least one additional agent.

Suitably, according to this embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

In a further aspect, the invention provides a method for preventing and/or treating a disease of the respiratory system in a subject, the method including the step of administering to the subject a therapeutically effective amount of the modified Ac-TMP-2 protein of the first-mentioned aspect (inclusive of fragments, variants and derivatives thereof), to thereby prevent and/or treat the disease of the respiratory system.

Suitably, the disease of the respiratory system is selected from the group consisting of asthma, emphysema, chronic bronchitis, and chronic obstructive pulmonary disease (COPD). Preferably, the disease of the respiratory system is asthma.

In one embodiment, this aspect further includes the step of administering to the subject at least one additional agent.

Suitably, according to the above embodiment, the at least one additional agent is selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

Preferably, the subject is a mammal.

More preferably, the subject is a human.

A further aspect of the invention provides a pharmaceutical composition comprising a therapeutically effective amount of the modified Ac-TMP-2 protein of the first-mentioned aspect (inclusive of fragments, variants and derivatives thereof), together with a pharmaceutically acceptable carrier, diluent or excipient.

In some embodiments, the pharmaceutical composition may further comprise at least one additional agent.

The at least one additional agent may be selected from the group consisting of nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof.

Suitably, the pharmaceutical composition is for preventing or treating inflammation and/or for preventing or treating a disease or condition associated with inflammation.

A yet further aspect of the invention provides an isolated nucleic acid that encodes the modified Ac-TMP-2 protein of the first-mentioned aspect (inclusive of fragments, variants and derivatives thereof).

A still yet further aspect of the invention provides a genetic construct comprising the isolated nucleic acid of the aforementioned aspect.

Another further aspect of the invention provides a host cell comprising the genetic construct of the aforementioned aspect.

Throughout this specification, unless the context requires otherwise, the words "comprise", "comprises" and "comprising" will be understood to imply the inclusion of a stated integer or group of integers but not the exclusion of any other integer or group of integers.

As used in this specification the indefinite articles "a" and "an" may refer to one entity or a plurality of entities (e.g. proteins) and are not to be read or understood as being limited to a single entity.

BRIEF DESCRIPTION OF THE FIGURES

FIG. 1. Amino acid sequence (SEQ ID NO: 1) of modified Ac-TMP-2 (N-terminal and C-terminal portion) and nucleotide sequence (SEQ ID NO:3). Vector-derived amino acid sequence and nucleotide sequence is bolded and restriction site-derived amino acid sequence and nucleotide sequence is double-underlined. The nucleotide sequence of SEQ ID NO: 3 is single underlined.

FIG. 2. Amino acid sequence of (i) modified Ac-AIP-2 (C-terminal portion, SEQ ID NO:2); (ii) modified Ac-AIP-$2_{Q48}$ (C-terminal portion, N-glycan mutant, SEQ ID NO:4); (iii) modified Ac-AIP-2 (N-terminal and C-terminal portion. SEQ ID NO: 1); and (iv) modified Ac-AIP-2 (N-terminal and C-terminal portion. N-glycan mutant. SEQ ID NO:5). Vector-derived amino acid sequence is bolded and restriction site-derived amino acid sequence is double-underlined. The amino acid sequence of Ac-AIP-2 (i.e., SEQ ID NOs:1, 2, 4 and 5) is single underlined.

FIG. 3. Purified recombinant native Ac-TMP-2 and modified Ac-TMP-2 (SEQ ID NO: 1) protect against TNBS-induced weight loss.

FIG. 4. Purified recombinant native Ac-TMP-2 and modified Ac-TMP-2 (SEQ ID NO: 1) protect against TNBS-induced colon pathology.

BRIEF DESCRIPTION OF THE SEQUENCES

Figure 5:
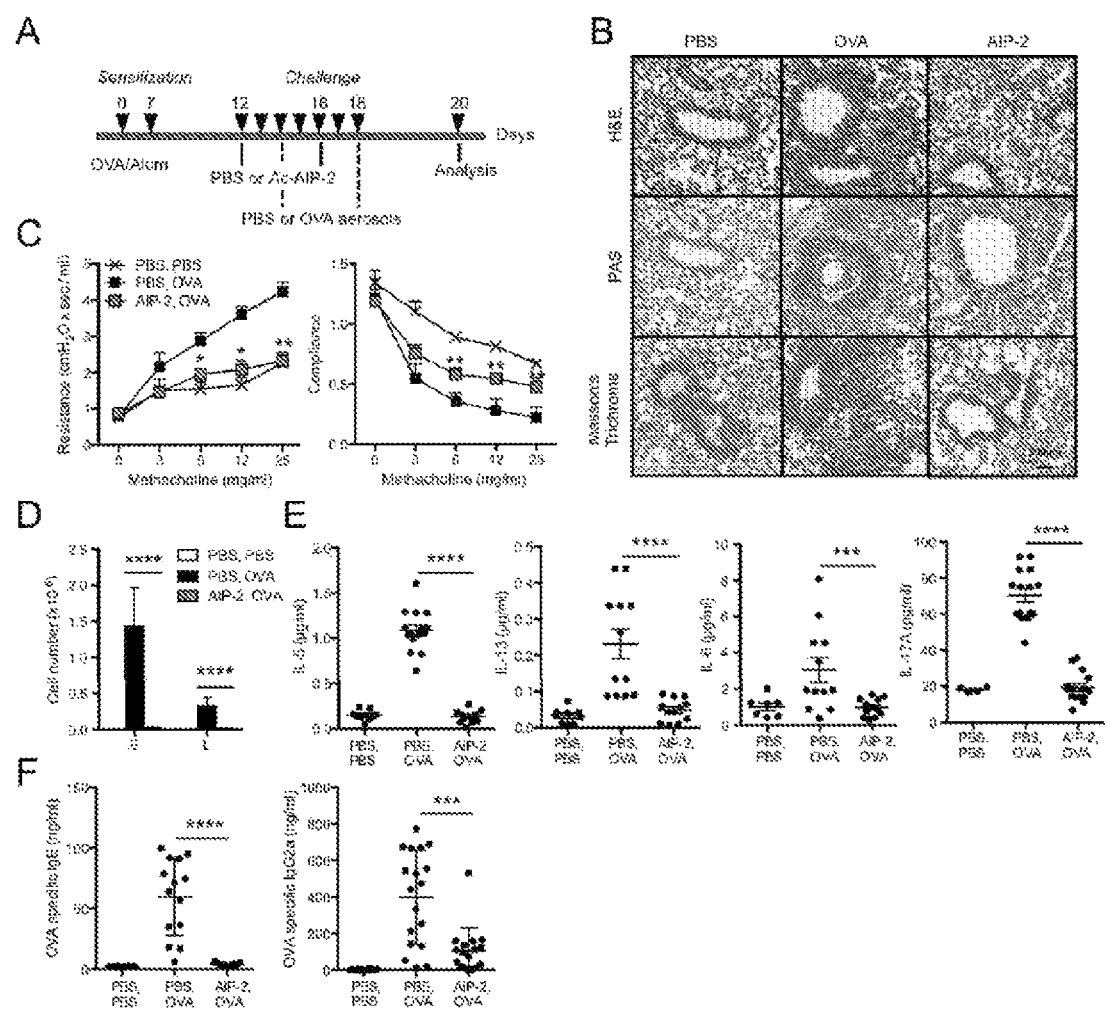
FIG. 5. Hookworm recombinant Ac-AIP-2 suppresses OVA-induced airway hyperresponsiveness, lung inflammation, mucus production and collagen deposition in mice. (A) Schematic representation of the experimental procedure. (B) Lung sections were stained with haematoxylin and eosin (H&E), Periodic Acid Schiff (PAS) or Masson's Trichrome. (C) Lung function assessed by invasive plethysmography measuring resistance and compliance in response to increasing doses of methacholine. (D) Frequencies of eosinophils (E) and lymphocytes (L) in the bronchoalveolar lavage fluid (BALF) were assessed by flow cytometry. (E) Concentrations of interleukin-5 (IL-5), IL-6, IL-13 and IL-17A in the lungs. (F) Levels of OVA-specific serum immunoglobulin (Ig)E and IgG2a. Results represent the mean of five independent experiments. *P≤0.05;  P≤0.01; * P≤0.001; **** P≤0.0001.

SEQ ID NO:1—Amino acid sequence of modified Ac-TMP-2 (N-terminal and C-terminal portions) in FIGS. 1 and 2 (Ac-AIP-2$_{NT}$). Amino acid sequence is single underlined.

SEQ ID NO:2—Amino acid sequence of modified Ac-TMP-2 (C-terminal portion) in FIG. 2 (Ac-AIP-2$_{WT}$). Amino acid sequence is single underlined.

SEQ ID NO:3—Nucleotide sequence of modified Ac-TMP-2 (N-terminal and C-terminal portions) in FIG. 1. Nucleotide sequence is single underlined.

SEQ ID NO:4—Amino acid sequence of modified Ac-TMP-2 (C-terminal portion, N-glycan mutant) in FIG. 2 (Ac-AIP-2$_{Q48}$). Amino acid sequence is single underlined.

SEQ ID NO:5—Amino acid sequence of modified Ac-TMP-2 (N-terminal and C-terminal portions. N-glycan mutant) in FIG. 2 (Ac-AIP-2$_{NTQ48}$). Amino acid sequence is single underlined.

DETAILED DESCRIPTION OF THE INVENTION

The present invention relates to methods for reducing, alleviating and/or preventing inflammation and/or inflammatory diseases or conditions such as asthma and/or inflammatory bowel disease.

The invention is at least partly predicated on the unexpected discovery that one or more proteins derivable or obtainable from hookworms including, but not limited to, *Ancylostoma caninum*, may be useful for reducing, alleviating and/or preventing inflammation and/or inflammatory diseases or conditions such as asthma and/or inflammatory bowel disease in a subject. These anti-inflammatory properties have also been shown to extend to particular modified versions of these hookworm proteins.

In particular aspects, the invention relates to a modified Ac-TMP-2 protein or a fragment, variant or derivative of the modified Ac-TMP-2 protein, for reducing, alleviating and/or preventing inflammation and/or inflammatory disease or conditions, such as asthma and/or inflammatory bowel disease. Suitably, the modified Ac-TMP-2 protein comprises a deletion or absence of a plurality of C-terminal amino acids usually present in an Ac-TMP-2 protein.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material includes material in native and recombinant form. The term "isolated" also encompasses terms such as "enriched", "purified" and/or "synthetic". Synthetic includes recombinant synthetic and chemical synthetic.

By "Ac-TMP-2" is meant tissue metalloprotease inhibitor-2, an excretory/secretory protein from *Ancylostoma caninum*. Ac-TMP-2 (UniProtKB/Swiss-Prot: # B1Q143) is a 244 amino acid polypeptide. Ac-TMP-2 or TMP-2 may also be referred to as Anti-Inflammatory Protein-2 (Ac-AIP-2, or AIP-2) herein.

As used herein, "modified", as in modified Ac-TMP-2, describes an isolated polypeptide or protein that comprises one or more N and/or C-terminal amino acid substitutions, insertions, additions and/or deletions, without limitation thereto, as compared to a wild-type or native Ac-TMP-2 protein. Suitably, one or a plurality of C-terminal amino acids may be lacking, absent or deleted without substantially diminishing anti-inflammatory activity. By way of a non-limiting example, a modified Ac-TMP-2 protein may lack one or a plurality of acidic C-terminal amino acids normally present in a wild-type or full length Ac-TMP-2 protein. The one or more acidic residues may include one or a plurality of glutamate (Glu or E), and/or aspartate (Asp or D) residues. For example, the truncated polypeptide or protein may lack at least 5, 10, 15, 20, 25, 30, 35, 40, 45, 50, 55, 60, 65, 70, 75, 80, 81, 82, 83, 84, 85, 86, 87, 88, 89, 90, 95 or more C-terminal amino acids, preferably including acidic residues, that are normally present in the full length or wild-type Ac-TMP-2 protein.

Suitably, the modified Ac-TMP-2 protein comprises a Netrin domain having some or all residues C-terminal of the Netrin domain deleted. Referring to SEQ ID NO:4 and 5, an example of such a modified Ac-TMP-2 protein terminates in the amino acid sequence DERD (SEQ ID NO:6), although without limitation thereto.

In an additional or alternative embodiment, one or more N-terminal amino acids may be lacking, deleted or absent. In some embodiments, the N terminal amino acids are of a signal peptide which may be deleted or replaced with a heterologous signal peptide amino acid sequence. The modified Ac-TMP-2 protein described herein may lack at least 1, 2, 3, 4, 5, 6, 7, 8, 9, 10, 11, 12, 13, 14, 15, 16, 17, 18, 19, 20 or more N-terminal amino acids.

Suitably, the modified Ac-TMP-2 protein comprises the amino acid sequence C—X—C at or near the N-terminus. In the amino acid sequences set forth in SEQ ID NO:1, SEQ ID NO:2, SEQ ID NO:4 and SEQ ID NO:5, this sequence is C—S—C. In this regard "at or near the N-terminus" means N-terminal or within about 1, 2, 3, 4, 5, 6, 7, 8, 9 or 10 amino acids of the N-terminus.

While not wishing to be bound by any particular theory, it is proposed that C-terminal amino acids may be deleted from wild-type Ac-TMP-2, alone or together with some N-terminal amino acids, as long as the C—X—C motif at or near the N-terminus is retained to allow insertion into the MMP active site cleft with subsequent inhibition of catalytic activity.

By way of a non-limiting example, modified Ac-TMP-2 may be a truncated polypeptide or protein, such as the modified Ac-TMP-2 of SEQ ID NO:1, SEQ ID NO:2, SEQ ID NO:4 and SEQ ID NO:5.

While the modified Ac-TMP-2 protein and the full length or wild-type Ac-TMP-2 protein may be referred to as tissue inhibitors of metalloproteases, it should be understood that the modified Ac-TMP-2 protein does not necessarily possess this particular biological activity. Furthermore, even if the modified Ac-TMP-2 protein has this biological activity, it is not necessarily essential or required for the anti-inflammatory properties of the protein.

It is further contemplated herein that modified polypeptides or proteins may be altered by crosslinking, fragmenting, denaturing, reducing disulfides, or attaching various prosthetic groups (e.g. PEGylation), albeit without limitation thereto.

As used herein, "fragment" describes a portion, domain, region or sub-sequence of a modified Ac-TMP-2 protein that comprises no more than 6, 10, 12, 15, 20, 30, 40, 50 60, 70, 80, 90, 100, 110, 120, 130, 140, 150, 160, 170, 180, 190, 200, 210 or 220 contiguous amino acids of the modified Ac-TMP-2 protein (such as set forth in SEQ ID NO:1. SEQ ID NO:2, SEQ ID NO:4 or SEQ ID NO:5).

Preferably, the fragment is a "biologically active fragment". In some embodiments, the biologically active fragment has no less than 10%, preferably no less than 25%, more preferably no less than 50%, and even more preferably no less than 75%, 80%, 85%, 90%, or 95% of the anti-inflammatory activity of modified Ac-TMP-2 protein (such as set forth in SEQ ID NO: 1, SEQ ID NO:2. SEQ ID NO:4 or SEQ ID NO:5). Such activity may be evaluated using standard testing methods and bioassays recognizable by the skilled artisan in the field as generally being useful for identifying such activity.

By "domain" (of a protein) is meant that part of a protein that shares common structural, physiochemical and functional features, for example hydrophobic, polar, globular, helical, or netrin-like (NTR) domains, or properties, for example a protein binding domain, a receptor binding domain, a co-factor binding domain, and the like.

Also contemplated are variants of the modified Ac-TMP-2 protein comprising one or more amino acid substitutions, insertions and/or deletions in the amino acid sequence of the modified Ac-TMP-2 protein or in a fragment thereof.

Typically, and in relation to proteins, a "variant" protein has one or more amino acids that have been replaced by different amino acids. It is well understood in the art that some amino acids may be changed to others with broadly similar properties without changing the nature of the activity of the protein (i.e., conservative substitutions).

In this regard, one or more amino acids may be altered to prevent or inhibit particular post-translational modifications, such as those produced by eukaryotic expression hosts including yeast and animal cells, as they may produce glycosylation patterns that are not identical to the human protein and thus, may ellicit immunogenic reactions in patients. A non-limiting example of a particular variant contemplated by the present invention is a non-glycosylated variant wherein an amino acid that is a site of glycosylation is deleted or replaced with another amino acid. For example, an N-linked glycosylation site may be mutated to a non-glycosylated amino acid, such as to a glutamine (Gln or Q) residue. For example, the yeast *S. cerevisiae* often produces high-mannose glycans which are immunogenic. In light of the foregoing, the N to Q mutation in modified Ac-TMP-2 of SEQ ID NOs:4 and 5 has been performed to remove a site for N-linked glycosylation in eukaryotic expression systems.

It will also be appreciated that one or more amino acid residues of a reference sequence, such as a modified Ac-TMP-2 protein, or fragment thereof, may be modified or deleted, or additional sequences added, without substantially altering the biological activity of the modified Ac-TMP-2 protein or fragment thereof. Such activity may be evaluated using standard testing methods and bioassays recognizable by the skilled artisan in the field as generally being useful for identifying such activity.

By way of example, the native signal peptide at the N-terminus of Ac-TMP-2 may be replaced in whole or part with a signal sequence specific to the expression system of choice, such as a yeast-specific signal sequence, to, for example, target secretion of the recombinantly expressed Ac-TMP-2 protein into the expression media.

The term "variant" includes peptidomimetics and orthologs of the modified Ac-TMP-2 protein. By "peptidomimetic" is meant a molecule containing non-peptidic structural elements that are capable of mimicking or antagonising the biological action(s) of a natural parent peptide. Examples of peptidomimetics include peptidic compounds in which the peptide backbone is substituted with one or more benzodiazepine molecules (see, e.g., James et al., *Science* 260:1937-42, 1993) and "retro-inverso" peptides (see, e.g., U.S. Pat. No. 4,522,752). The term also refers to a moiety, other than a naturally occurring amino acid, that conformationally and functionally serves as a substitute for a particular amino acid in a protein without adversely interfering to a significant extent with the function of the protein. Examples of amino acid mimetics include D-amino acids. Proteins substituted with one or more D-amino acids may be made using well known peptide synthesis procedures. Additional substitutions include amino acid analogs having variant side chains with functional groups, such as, for example, β-cyanoalanine, canavanine, djenkolic acid, norleucine, 3-phosphoserine, homoserine, dihydroxyphenylalanine, 5-hydroxytryptophan, 1-methylhistidine, and 3-methylhistidine.

By "orthologs" of the modified Ac-TMP-2 protein is meant modified TMP orthologs from other intestinal helminths (i.e., hookworms, whipworms and roundworms), including human hookworms, such as, for example, *Necator americanus, Ancylostonma duodenale* and *Ancylosloma ceylanicum*, and pig whipworms, such as, for example, *Trichuris suis* and *Trichuris trichiura*.

In one embodiment, a protein variant or ortholog shares at least 70%, preferably at least 75%, 80% or 85% and more preferably at least 90%, 91%, 92%, 93%, 94%, 95%, 96%, 97%, 98%, or 99% sequence identity with a reference amino acid sequence such as SEQ ID NO: 1, SEQ ID NO:2. SEQ ID NO:4 or SEQ ID NO:5.

Preferably, sequence identity is measured over at least 60%, more preferably over at least 75%, more preferably over at least 90% or more preferably over at least 95%, 98% or substantially the full length of the reference sequence comprising the amino acid sequence of SEQ ID NO:1. SEQ ID NO:2, SEQ ID NO:4 or SEQ ID NO:5.

In order to determine percent sequence identity, optimal alignment of amino acid and/or nucleotide sequences may be conducted by computerised implementations of algorithms (Geneworks program by Intelligenetics: GAP, BEST-FIT, FASTA, and TFASTA in the Wisconsin Genetics Software Package Release 7.0, Genetics Computer Group, WI, USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389-402, 1997.

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

Variant proteins can be produced by a variety of standard, mutagenic procedures known to one of skill in the art. A mutation can involve the modification of the nucleotide sequence of a single gene, blocks of genes or a whole chromosome, with the subsequent production of one or more mutant proteins. Changes in single genes may be the consequence of point mutations, which involve the removal, addition or substitution of a single nucleotide base within a DNA sequence, or they may be the consequence of changes involving the insertion or deletion of large numbers of nucleotides.

Mutations occur following exposure to chemical or physical mutagens. Such mutation-inducing agents include ionizing radiation, ultraviolet light and a diverse array of chemical agents, such as alkylating agents and polycyclic aromatic hydrocarbons, all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation, which can subsequently be reflected at the protein level. Mutation also can be site-directed through the use of particular targeting methods.

Mutagenic procedures of use in producing modified Ac-TMP-2 comprising one or more mutations include, but are not limited to, random mutagenesis (e.g., insertional mutagenesis based on the inactivation of a gene via insertion of a known DNA fragment, chemical mutagenesis, radiation mutagenesis, error prone PCR (Cadwell and Joyce, *PCR Methods Appl.* 2:28-33, 1992)) and site-directed mutagenesis (e.g., using specific oligonucleotide primer sequences that encode the DNA sequence of the desired mutation). Additional methods of site-directed mutagenesis are disclosed in U.S. Pat. Nos. 5,220,007; 5,284,760; 5,354,670; 5,366,878; 5,389,514; 5,635,377; and 5,789,166.

Also provided are "derivatives" of the modified proteins, including fragments and variants thereof. Such derivatives may include chemically modified proteins (e.g amino acid side chain modifications), chemically cross-linked proteins, proteins modified to include avidin, biotin and other binding moieties, addition of eptiope tags and/or fusion partners (e.g FLAG, haemagglutinin, myc tags, GST or MBP, hexahistidine fusion partners), labels (e.g. radioactive labels, fluorescent labels) and enzymes (e.g HRP, alkaline phosphatase), although without limitation thereto.

The modified Ac-TMP-2 protein (inclusive of fragments, variants and derivatives) can be prepared by any suitable procedure known to those of skill in the art.

In one embodiment, the modified Ac-TMP-2 protein (inclusive of fragments, variants and derivatives) are produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2001) for examples of suitable methodology.

In another embodiment, the modified Ac-TMP-2 protein, (inclusive of fragments, variants and derivatives) is prepared as a recombinant protein.

While production of recombinant proteins is well known in the art, the skilled person may refer to standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-1999), in particular Chapters 10 and 16; and CURRENT PROTOCOLS IN PROTEIN SCIENCE Eds. Coligan et al., (John Wiley & Sons, Inc. 1995-1999), in particular Chapters 1, 5 and 6.

Accordingly, in another aspect the invention provides an isolated nucleic acid that encodes a modified Ac-TMP-2 protein (such as set forth in SEQ ID NO:1, SEQ ID NO:2, SEQ ID NO:4 or SEQ ID NO:5) or fragment, variant or derivative of the modified Ac-TMP-2 protein.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylcytosine, methylinosine, methyladenosine and/or thiouridine, although without limitation thereto.

Accordingly, in particular embodiments, the isolated nucleic acid is cDNA.

In further embodiments, the isolated nucleic acid is codon-optimised nucleic acid.

The invention also provides a genetic construct comprising the isolated nucleic acid of the aforementioned aspect.

The invention further provides a host cell comprising the genetic construct of the aforementioned aspect.

Suitably, the genetic construct comprises one or more additional nucleotide sequences which facilitate expression of the isolated nucleic acid. Such additional nucleotide sequences may include regulatory sequences such as a promoter, enhancer, polyadenylation sequence, splice donor/acceptor sequences, selection marker (e.g. for antibiotic resistance), signal peptide, origin of replication or other nucleotide sequences that assist transformation, propagation, selection and expression in prokaryotic and/or eukaryotic host cells. In the context of recombinant protein expression, it will be understood by persons skilled in the art that the appropriate genetic construct and host cell will be to some extent interdependent. Introduction of the genetic construct into prokaryotic and/or eukaryotic host cells, propagation and selection of protein-expressing cells is well known in the art.

Suitable host cells for expression may be prokaryotic or eukaryotic. For example, suitable host cells may be mammalian cells (e.g. HeLa, HEK293T, Jurkat cells), yeast cells (e.g. *Saccharomyces cerevisiae*), insect cells (e.g. Sf9, *Trichoplusia ni*) utilized with or without a baculovirus expression system, or bacterial cells, such as *E. coli*, or a *Vaccinia* virus host.

In one aspect, the invention provides a method of reducing or alleviating inflammation in a subject, the method including the step of administering to the subject a therapeutically effective amount of a modified Ac-TMP-2 protein or a fragment, variant or derivative of the modified Ac-TMP-2 protein.

In another aspect, the invention provides a method of preventing inflammation in a subject, the method including the step of administering to the subject a therapeutically effective amount of a modified Ac-TMP-2 protein or a fragment, variant or derivative thereof.

By "reducing", as in reducing inflammation in a subject, is meant a lessening or shortening of a symptom, aspect, or characteristic associated with inflammation (e.g., redness, heat, swelling, and/or pain), or of the length of time a subject experiences a symptom, aspect, or characteristic associated with inflammation. Such reducing need not be absolute to be beneficial to the subject. By "alleviating", as in alleviating inflammation in a subject, is meant a reduction in the severity or seriousness of a symptom, aspect, or characteristic associated with inflammation (e.g., redness, heat, swelling, and/or pain). Such alleviating need not be absolute to be beneficial to the subject. Reduction and/or alleviation of inflammation in a subject can be determined using any methods or standards known to the ordinarily skilled artisan, including both qualitative and quantitative methods and standards.

It is to be understood that reducing or alleviating inflammation in a subject is a method of treating inflammation in the subject. As used herein, "treating" (or "treat" or "treatment") refers to a therapeutic intervention that ameliorates a sign or symptom of inflammation after it has begun to develop. The term "ameliorating", with reference to inflammation, refers to any observable beneficial effect of the treatment. The beneficial effect can be determined using any methods or standards known to the ordinarily skilled artisan.

As used herein, "preventing" (or "prevent" or "prevention") refers to a course of action (such as administering a therapeutically effective amount of modified Ac-TMP-2 or a fragment, variant or derivative thereof) initiated prior to the onset of a symptom, aspect, or characteristic of inflammation so as to prevent or reduce the symptom, aspect, or characteristic. It is to be understood that such preventing need not be absolute to be beneficial to a subject. A "prophylactic" treatment is a treatment administered to a subject who does not exhibit signs of inflammation or exhibits only early signs for the purpose of decreasing the risk of developing a symptom, aspect, or characteristic of inflammation.

As used herein, "inflammation" refers to the well known localised response to various types of injury or infection, which is characterised by redness, beat, swelling, and pain, and often also including dysfunction or reduced mobility. Inflammation represents an early defense mechanism to contain an infection and prevent its spread from the initial focus. Major events in inflammation include dilation of capillaries to increase blood flow, changes in the microvasculature structure, leading to escape of plasma and proteins and leukocytes from the circulation, and leukocyte emigration from the capillaries and accumulation at the site of injury or infection.

Inflammation is often associated with, or secondary to, a disease, disorder and/or condition in a subject, including an immunological disease, disorder and/or condition (such as an autoimmune disease, disorder and/or condition) and allergic reactions. Exemplary immunological diseases, disorders and/or conditions include, without limitation, Addison's disease, ankylosing spondylitis, celiac disease, chronic inflammatory demyelinating polyneuropathy (CIDP), chronic recurrent multifocal ostomyclitis (CRMO), Crohn's disease, demyelinating neuropathies, glomerulonephritis. Goodpasture's syndrome, Graves' disease, Guillain-Barre syndrome, Hashimoto's encephalitis, Hashimoto's thyroiditis, hypogammaglobulinemia, idiopathic thrombocytopenic purpura (ITP), insulin-dependent diabetes (type1), juvenile arthritis, Kawasaki syndrome, multiple sclerosis, myasthenia gravis, postmyocardial infarction syndrome, primary biliary cirrhosis, psoriasis, idiopathic pulmonary fibrosis. Reiter's syndrome, rheumatoid arthritis, sarcoidosis, scleroderma. Sjogren's syndrome, systemic lupus erythematosus (SLE), thrombocytopenic purpura (TTP), ulcerative colitis, vasculitis, vitiligo, and Wegener's granulomatosis.

As will be understood by one of ordinary skill in the art, diseases of the digestive tract (e.g., chronic gastritis or an inflammatory bowel disease, such as, Crohn's disease or ulcerative colitis) and diseases of the respiratory system (e.g., asthma, emphysema, chronic bronchitis, and chronic obstructive pulmonary disease (COPD)) have an inflammatory component, and thus are particularly amenable to treatment using the disclosed methods.

Accordingly, in one aspect, the invention resides in a a method for preventing and/or treating an inflammatory bowel disease in a subject, the method including the step of administering to the subject a therapeutically effective amount of the modified Ac-TMP-2 protein hereinbefore described, to thereby prevent and/or treat the inflammatory bowel disease.

In one embodiment, the inflammatory bowel disease is Crohn's disease or ulcerative colitis.

In a related aspect, the invention resides in a method for preventing and/or treating a disease of the respiratory system in a subject, the method including the step of administering to the subject a therapeutically effective amount of the modified Ac-TMP-2 protein hereinbefore described, to thereby prevent and/or treat the disease of the respiratory system.

In particular embodiments, the disease of the respiratory system is selected from the group consisting of asthma, emphysema, chronic bronchitis, and chronic obstructive pulmonary disease (COPD). In a particular preferred embodiment, the disease of the respiratory system is asthma.

As will also be understood by one of ordinary skill in the art, inflammation that is associated with, or secondary to, a disease, disorder and/or condition in a subject, often occurs when the disease, disorder and/or condition is refractory to a baseline therapy, for example, a baseline therapy comprising nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents), antibiotics, and combinations thereof. By "refractory" is intended resistance to treatment, particularly first line treatment.

The term "subject" includes both human and veterinary subjects. For example, administration to a subject can include administration to a human subject or a veterinary subject. Preferably, the subject is a human. However, therapeutic uses according to the invention may also be applicable to mammals such as domestic and companion animals, performance animals such as horses, livestock, and laboratory animals.

By "administration" is intended the introduction of a composition (e.g., a pharmaceutical composition comprising a modified Ac-TMP-2 protein, or a fragment, variant or derivative thereof, into a subject by a chosen route.

The term "therapeutically effective amount" describes a quantity of a specified agent sufficient to achieve a desired effect in a subject being treated with that agent. For example, this can be the amount of a composition comprising modified Ac-TMP-2 (or a fragment, variant or derivative thereof) necessary to reduce, alleviate and/or prevent inflammation. In some embodiments, a "therapeutically effective amount" is sufficient to reduce or eliminate a symptom of inflammation. In other embodiments, a "therapeutically effective amount" is an amount sufficient to achieve a desired biological effect, for example an amount that is effective to decrease redness, heat, swelling, and/or pain associated with inflammation.

Ideally, a therapeutically effective amount of an agent is an amount sufficient to induce the desired result without causing a substantial cytotoxic effect in the subject. The effective amount of an agent, for example modified Ac-TMP-2 (or a fragment, variant or derivative thereof), useful for reducing, alleviating and/or preventing inflammation will be dependent on the subject being treated, the type and severity of any associated disease, disorder and/or condition, and the manner of administration of the therapeutic composition.

A therapeutically effective amount of a composition comprising a modified Ac-TMP-2 protein (or a fragment, variant or derivative thereof) may be administered in a single dose, or in several doses, for example daily, during a course of treatment. However, the frequency of administration is dependent on the preparation applied, the subject being treated, the severity of inflammation, and the manner of administration of the therapy or composition.

In some embodiments, the modified Ac-TMP-2 protein or fragment, variant or derivative thereof may further comprise a fusion partner amino acid sequence. The fusion partner amino acid sequence is advantageously encoded by the genetic construct to be expressed at the N- and/or C-terminus of the recombinant protein. Fusion partners include polyhisitidine (e.g $His_6$), maltose binding protein (MBP), glutathione-S-transferase (GST) and epitope tags such as FLAG, HA and myc tags. Fusion partners facilitate identification and purification of recombinantly-expressed proteins by way of affinity resins (e.g. metal ions, maltose, glutathione resins) or antibodies in the case of epitope tags.

In certain embodiments, the method of treating or preventing inflammation and/or the pharmaceutical composition may comprise one or more additional agents suitable for administration to the subject. Various combinations of one or more additional agents as known by one of skill in the art for reducing, alleviating and/or preventing inflammation (and/ or for treating or preventing a disease, disorder and/or condition associated with inflammation) may be administered to a subject in need thereof in addition to a therapeutically effective amount of a modified Ac-TMP-2 protein (or a fragment, variant or derivative thereof). That is, one or more additional agents traditionally used for the treatment and/or prevention of inflammation may be administered to a subject in addition to a therapeutically effective amount of a modified Ac-TMP-2 protein (or a fragment, variant or derivative thereof).

For example, nonsteroidal anti-inflammatory drugs (NSAIDs), aminosalicylates, corticosteroids, immunosuppressants, anti-cytokine/cytokine receptor agents (e.g., anti-TNFα agents, anti-IL-5 agents, anti-IL-13 agents, anti-IL-17 agents, and anti-IL-6R agents) particularly anti-cytokine/ cytokine receptor antibodies, antibiotics, and combinations thereof can be administered with modified Ac-TMP-2 protein (or a fragment, variant or derivative thereof) in certain embodiments for reducing, alleviating and/or preventing inflammation.

In certain embodiments, the one or more additional agents provide a conserving effect on the modified Ac-TMP-2 protein (or a fragment, variant or derivative thereof). In further embodiments, the modified Ac-TMP-2 protein (or a fragment, variant or derivative thereof) provide a conserving effect on the one or more additional agents. In still further embodiments, the one or more additional agents provide a complimentary effect to the action of the modified Ac-TMP-2 protein (or a fragment, variant or derivative thereof), preferably eliminating or reducing the frequency or severity of (and/or preventing) one or more symptoms associated with inflammation.

As is well known to one of skill in the art, nonsteroidal anti-inflammatory drugs (NSAIDs), also referred to as non-steroidal anti-inflammatory agents (NSAIAs), are drugs with analgesic, antipyretic and anti-inflammatory effects, and include salicylates (e.g., aspirin) and propionic acid derivatives (e.g., ibuprofen and naproxen).

Aminosalicylates are well known in the art for use in the treatment of inflammatory bowel disease (particularly ulcerative colitis), and include, for example, balsalazide, mesalazine, olsalazine, and sulfasalazine.

As is well known to one of skill in the art, corticosteroids are drugs that closely resemble cortisol, a hormone produced by the adrenal glands. Exemplary corticosteroids include, without limitation, cortisone, prednisone, prednisolone, and methylprednisolone.

Immunosuppressants are well known in the art for use in the treatment of inflammation associated with certain diseases or conditions, and include, for example, the drugs ciclosporin, azathioprine and mycophenolate.

As is well known to one of skill in the art, anti-cytokine/cytokine receptor agents (e.g., anti-TNFα agents, anti-IL-5 agents, anti-IL-13 agents, anti-IL-17 agents, and anti-IL-6R agents) include, without limitation, small molecule inhibitors and antibodies.

In some embodiments, the combination of a modified Ac-TMP-2 (or a fragment, variant or derivative thereof) and one or more additional agents produces a synergistic effect in the treatment and/or prevention of inflammation.

Accordingly, the present invention also includes a method of enhancing the therapeutic effectiveness of an agent in treating any condition for which such agents are used (e.g., inflammation and any associated disease, disorder and/or condition).

In one embodiment, the modified Ac-TMP-2 protein (or a fragment, variant or derivative thereof) is administered prior to the administration of the one or more additional agents. In another embodiment, the modified Ac-TMP-2 (or a fragment, variant or derivative thereof) is administered after the administration of the one or more additional agents. In still another embodiment, the modified Ac-TMP-2 protein (or a fragment, variant or derivative thereof) is administered simultaneously with the administration of the one or more additional agents. In yet another embodiment, administration of the modified Ac-TMP-2 protein (or a fragment, variant or derivative thereof) and the administration of the one or more additional agents (either sequentially or concurrently) results in reduction or alleviation of inflammation that is greater than such reduction or alleviation from administration of either the modified Ac-TMP-2 protein (or a fragment, variant or derivative thereof) or one or more additional agents in the absence of the other.

The modified Ac-TMP-2 protein (or a fragment, variant or derivative thereof) and one or more additional agents can be administered by any conventional method/route available for use in conjunction with therapeutic compositions, as is well known to one of skill in the art. Such methods include, without limitation, administration by way of microneedle injection into specific tissue sites, such as described in U.S. Pat. No. 6,090,790, topical creams, lotions or sealant dressings applied to sites of inflammation, such as described in U.S. Pat. No. 6,054,122 or implants which release the modified Ac-TMP-2 (or a fragment, variant or derivative thereof) such as described in International Publication WO 99/47070.

In this regard, compositions comprising a modified Ac-TMP-2 protein (or a fragment, variant or derivative thereof) and, optionally, one or more additional agents, may be administered in association with, or as a component of, a biomaterial, biopolymer, inorganic material such as hydroxyapatite or derivates thereof, surgical implant, prosthesis, wound dressing, compress, bandage, or the like suitably impregnated, coated or otherwise comprising the composition.

Suitably, the composition comprises an appropriate pharmaceutically-acceptable carrier, diluent or excipient.

Preferably, the pharmaceutically-acceptable carrier, diluent or excipient is suitable for administration to mammals, and more preferably, to humans.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, and pyrogen-free water.

A useful reference describing pharmaceutically acceptable carriers, diluents and excipients is Remington's Pharmaceutical Sciences (Mack Publishing Co. NJ USA, 1991).

Any safe route of administration may be employed for providing a subject with compositions comprising a modified Ac-TMP-2 protein (or a fragment, variant or derivative thereof) and, optionally, one or more additional agents. For example, oral, rectal, parenteral, sublingual, buccal, intravenous, intra-articular, intra-muscular, intra-dermal, subcutaneous, inhalational, intra-nasal, intraocular, intraperitoneal, intracerebroventricular, transdermal, and the like may be employed.

Dosage forms include tablets, dispersions, suspensions, injections, solutions, syrups, troches, capsules, suppositories, aerosols, transdermal patches, and the like. These dosage forms may also include injecting or implanting controlled releasing devices designed specifically for this purpose or other forms of implants modified to act additionally in this fashion. Controlled release of a modified Ac-TMP-2 protein (or a fragment, variant or derivative thereof) and, optionally, one or more additional agents, may be effected by coating the same, for example, with hydrophobic polymers including acrylic resins, waxes, higher aliphatic alcohols, polylactic and polyglycolic acids, and certain cellulose derivatives such as hydroxypropylmethyl cellulose. In addition, the controlled release may be affected by using other polymer matrices, liposomes and/or microspheres.

The above compositions may be administered in a manner compatible with the dosage formulation, and in such amount as is pharmaceutically/therapeutically-effective. The dose administered to a subject, in the context of the present invention, should be sufficient to effect a beneficial response (e.g., a reduction in inflammation) in a subject over an appropriate period of time. The quantity of a modified Ac-TMP-2 protein (or a fragment, variant or derivative thereof) to be administered may depend on the subject to be treated, inclusive of the age, sex, weight and general health condition thereof, factors that will depend on the judgement of a practitioner of ordinary skill in the art.

Compositions as described herein may also include expression vectors, such as viral vectors (e.g., vaccinia, adenovirus and adenovirus-associated viruses (AAV), retroviral and lentiviral vectors, and vectors derived from herpes simplex virus and cytomegalovirus. Gene therapy is also applicable in this regard, such as according to methods set forth in U.S. Pat. Nos. 5,929,040 and 5,962,427.

So that the invention may be readily understood and put into practical effect, the following non-limiting Examples are provided.

EXAMPLES

Example 1

Recombinant Modified Ac-TMP-2 Suppresses IBD (TNBS Model)

Animals and TNBS-Induced Colitis

Six week old male Swiss C57Bl/6 mice (weight 20-25 g, Animal Resources Centre, Perth. Western Australia) were allowed to adapt for seven days before they were used in the experiments. They were housed according to Australian animal rights and regulations standards. All procedures involving mice were approved by the James Cook University Animal Ethics Committee.

Colitis was induced by intraluminal injection of TNBS as described by Neurath et al. (*J Exp Med.* 182:1281-90, 1995). Briefly, mice were fasted for 24 hours with free access to drinking water. They were anesthetized i.p. by a mixture of ketamine (50 µg/kg) and xylazine (5 µg/kg). Next, 100 µL of a 2.5 mg TNBS in 45% ethanol solution was injected intrarectally through a flexible catheter of 3.2 cm length. After TNBS injection, mice were held upside down in a 45° position for one minute to prevent leakage of the TNBS solution and were replaced in their cages with free access to food and water afterward.

Experimental Protocol

On day 0, mice received a single intraperitoneal injection with 20 µg of native Ac-TMP-2, Trunc-Ac-TMP-2 (SEQ ID NO: 1) or a mock PBS injection. Five hours later, they received an intrarectal injection with 2.5 mg of TNBS in 45% ethanol, under a mild anaesthetic. From day 0 to day 3, mice were monitored daily for weight loss. On day 3, mice were euthanized and colons were collected for assessment of inflammation (colon length, wall thickening, oedema, and ulceration).

Results

Modified Ac-TMP-2 is shown in FIG. 1. In work leading up to the present invention, the C-terminal amino acid sequence GLEQKLISEEDLNSAVD was deleted from wild-type Ac-TMP2 together with the N-terminal sequence EAE-AEF. Deletion of these was studied in light of the inventor's idea that TIMPs seem to require the C—X—C motif at the N-terminus to allow insertion into the MMP active site cleft and subsequent inhibition of catalytic activity. Both native Ac-TMP-2 and modified (i.e truncated) Ac-TMP-2 significantly protected mice from weight loss as shown as absolute weight loss (FIG. 3A) and percent weight loss (FIG. 3B) plotted as the mean for each group of mice when compared to the TNBS group that received the mock injection.

Trunc-Ac-TMP-2 was further assessed for colon length (FIG. 4A) and microscopic score (FIG. 4B). For both measures, native Ac-TMP-2 and truncated Ac-TMP-2 afforded a significant reduction in intestinal pathology (FIG. 4). This protective effect of Trunc-Ac-TMP-2 is also evident grossly in colons from Naïve (A), TNBS (B). Native-Ac-TMP-2 (C) and Trunc-Ac-TMP-2 (D) treated mice in FIG. 4C.

Therefore, Trunc-Ac-TMP-2 demonstrates similar protective properties in a mouse model of IBD than native Ac-TMP-2.

Example 2

Recombinant Modified Ac-TMP-2 (AIP-2) Suppresses Asthma

Materials and Methods

Mice.

3-12 week old BALB/c.ARC mice were purchased from Animal Resource Center (Perth. Australia) and housed under SPF conditions according to the Australian animal rights and regulation standards. MyD88-TRIFF KO mice, kindly provided by S. Akira (Osaka University, Japan) via L. Schofield from Walter and Eliza Hall Institute (Melbourne, Australia), and DEREG mice (25) were bred in the animal facility at James Cook University (JCU), Cairns, QLD, Australia. All experimental protocols were approved by the JCU Animal Ethics Committee.

Reagents.

*A. caninunm* adult hookworms were cultured as previously described (16). The supernatant (AcES) was collected and endotoxin removed using one of two methods, Endotrap Blue (Hyglos) according to the manufacturer's instructions or Triton X-114 (Sigma) as previously described with some minor changes (16). Recombinant Ac-AIP-2 was expressed as a secreted protein in the yeast *Pichia pastoris* using methods described elsewhere (31). The cDNA encoding the mature sequence of Ac-AIP-2 (amino acids 17-244) was cloned in frame into pPICZαA (Invitrogen) using EcoRI and XbaI restriction sites. The recombinant plasmids were linearized by SacI digestion and transformed into *P. pastoris* strain X-33 by electroporation according to the manufacturer's instructions (Invitrogen). The transformants were selected on yeast extract-peptone-dextrose plates containing zeocin and assessed for expression of recombinant protein via Western blot. A Western positive clone was grown in a shaker flask, and expression of the recombinant 6×His tagged Ac-AIP-2 was induced with methanol, as per the manufacturer's instructions (Invitrogen). The recombinant fusion protein was purified with a nickel affinity column and eluates containing Ac-AIP-2 were concentrated using Amicon Ultra Centrifugal concentrators and buffered exchanged into PBS pH 7.4. Lipopolysaccharide contents in AcES and Ac-AIP-2 were below 5 ng/mg as determined using the Limulus Amoebocyte Lysate (LAL) assay (Pierce). AIP-2 was denatured by trypsin digestion (1 µg/ml) (Sigma) and heat denaturation as described previously (16). AIP-2 was labelled with Alex Fluor 647 using a protein labelling kit following manufacturer's instructions (Life Technologies). House Dust Mite extract was purchased from Monoclonal antibodies to CD3, CD4, CD25, CD19, B220, 120G8, TCR, Foxp-3, CCR9, CD103, CTLA-4, F4/80, Siglec-F, Gr-1, CD11c, CD11b, IA/IE, CD80, CD86, IL-4, IL-5, IL-10, and IL-17A were purchased from ebiosciences and BD Biosciences.

AcES or AIP-2 Treatment and Induction of Allergic Asthma.

Sensitization was performed by 2 i.p. injections of 20 µg of endotoxin free OVA (Hyglos) in 2 mg of Aluminium hydroxide (Alum) (Pierce) at days 0 and 7. On days 12 to 16, mice were treated with 1 mg/kg of AcES or AIP-2 in PBS (Life Technologies, Australia). From days 14-18, mice were either exposed to a daily OVA (0.2%) (Sigma) or PBS aerosol for 20 min using an ultrasonic nebulizer (Ventalair Max, Allersearch). On day 20, mice were analyzed for lung function and the hallmarks of allergic airway disease.

Airway Hyperresponsiveness.

Invasive measurements of dynamic lung resistance and compliance were performed two days after the last aerosol challenge using Flexivent (SCIREQ, Emka Technologies) as previously described (32). Briefly, mice were anesthetized (50 mg/kg of Ketamine and 5 mg/kg of Xylazine) tracheotomized, and immediately intubated with an 18-G catheter, followed by mechanical ventilation. Respiratory frequency was set at 150 breaths/min with a tidal volume of 0.2 ml, and a positive-end expiratory pressure of 2 ml $H_2O$ was applied. Increasing concentrations of methacholine (0-50 mg/ml) were administered at a rate of 20 puffs per 10 seconds, with each puff of aerosol delivery lasting 10 ms, via a nebulizer aerosol system with a 2.5-4.0 µm aerosol particle size generated by a nebulizer head (Aeroneb, Aerogen). Baseline resistance was restored before administering subsequent doses of methacholine.

Analysis of BALF Cells.

Mice were bled by severing the caudal vena cava, and a cannula was inserted into the trachea. Lungs were washed 3 times with 1 ml of warmed PBS. For differential BALF cell counts, cells were stained with anti-Siglec-f, anti-Gr1, anti-CD3 and anti-CD19 mAbs (BD Biosciences) and analyzed by flow cytometry using a FACS Canto II flow cytometer and FACS Diva software. Eosinophils were defined as Siglec-F$^+$ CD3$^-$CD19$^-$, neutrophils as Gr-1$^{high}$ CD3$^-$CD19$^-$, lymphocytes as CD3$^+$CD19$^+$ and alveolar macrophages as large autofluorescent cells.

Serum Antibody Measurements.

Serum OVA-specific IgG2a and IgE were measured by ELISA. Antigen-coated Maxisorp plates (Nunc) were incubated with serial dilutions of sera and biotinylated anti-IgG2a or anti-IgE mAbs (BD). HRP-conjugated streptavidin (BD Biosciences) and TMB (KPL) were used for detection.

Cytokine Assays.

Lung samples were homogenized in calcium- and magnesium-free Hank's Balanced Salt Solution and phosphatases and proteases inhibitor cocktail (Roche). Multiplex IL-5, IL-13, IL-17A and IFN-analyses were performed with cytokine bead arrays (CBA) using FACS array (BD Biosciences).

Tissue Processing.

Trachea, lungs, mesenteric lymph nodes (MLN), peripheral lymph nodes (brachial, inguinal, and popliteal) or spleens were processed in RPMI 1640 media containing 2% fetal calf serum (FCS), 400 U type I collagenase and 1 mg/ml DNAse I (Life Technologies) using Miltenyi GentleMACS and incubated for 15 min at 37° C. Cells were strained through a 70 µm cell strainer. Erythrocytes were lysed with ACK lysis buffer. siLP were obtained after digestion in RPMI containing 5% FCS, 5 mM EDTA, and 2 mM dithiothreitol (DTT) as described previously (33).

Briefly. Peyer's patches were removed and tissue pieces were incubated under agitation for 30 min. Intestinal epithelial lymphocytes were discarded by filtration and the remainder was further incubated in RPMI containing 5% FCS, 400 U type I collagenase and 1 mg/ml DNAse I for 30 min at 37° C. Small intestine lamina propria cells were filtered and stained for flow cytometry.

Intestinal Surgery.

Three week old BALB/c.ARC mice were anaesthetized with Ketamine (50 mg/kg) and Xylazine (5 mg/kg) and the MLN of the small and large intestine were removed as described previously (26). For MLN resection (MLNrx) experiments, intestines were placed back into the abdomen after MLN removal. For MLN transplant (MLNtx) experiments. MLN were isolated from AIP-2 or PBS treated donors. The MLN of the small and large intestine of the host were removed and donor MLN were transplanted into this region. Mice were allowed to recover for 6 weeks prior to subsequent experiments.

Statistical Analyses.

ANOVA for repeated measures was used to determine the levels of difference between groups of mice for plethysmography measurements. Comparisons for all pairs were performed by unpaired two-tailed Student's t-test. Significance levels were set at a P value of 0.05.

Results and Discussion

Immunoepidemiological observations have highlighted the protective effect of helminth infections against allergies (1-3). One such study including almost 13.000 individuals in rural Ethiopia found that the risk of wheeze was independently reduced by infection with the hookworm *Necator americanus* but unrelated to viral exposure (4). More recently, the efficacy of experimental infections with *N. americanus* or the pig whipworm *Trichuris suis* has been assessed in clinical trials for inflammatory bowel disease (5-7), multiple sclerosis (8), asthma (9) and rhinitis (2). We recently completed an open-label clinical trial where experimental low-dose hookworm infection was coupled with gluten microchallenge to dramatically improve the gluten tolerance of celiac disease sufferers (10). Improved tolerance to gluten coincided with decreased frequency of IFN-γ producing intestinal epithelial cells and increased frequency of Foxp3 regulatory T cells ($T_{reg}$) in the gut. While probiotic worm therapy has generated substantial interest in the treatment of chronic inflammatory conditions (11), concerns prevail around the implications of experimental human infection with a live pathogen (12), and its potential scalability as a therapeutic modality. Identifying protective worm molecules could circumvent this issue and promote the development of helminth-derived biologics for treating a range of disorders that result from a dysregulated immune system. Very few worm-derived immunomodulatory molecules have been characterized, and even fewer have been demonstrated to protect against inflammatory diseases in mice (13, 14). We previously showed that hookworm excretory/secretory products (AcES) modulated chemically induced colitis in mice, and that protective moieties were proteins (15, 16). Herein, we show that AcES protects against experimental asthma and that this protection is likely due, at least in part, to the secretion of a protein that we have termed AIP-2. We show that recombinant AIP-2 induces the expansion of mesenteric CD103$^+$ dendritic cells, resulting in the generation of $T_{reg}$ that home to the mucosa. Moreover, we show that AIP-2 generates a pro-regulatory imprint on mesenteric lymphoid tissues, promoting long-term specific protection against allergic asthma.

Figure 9:
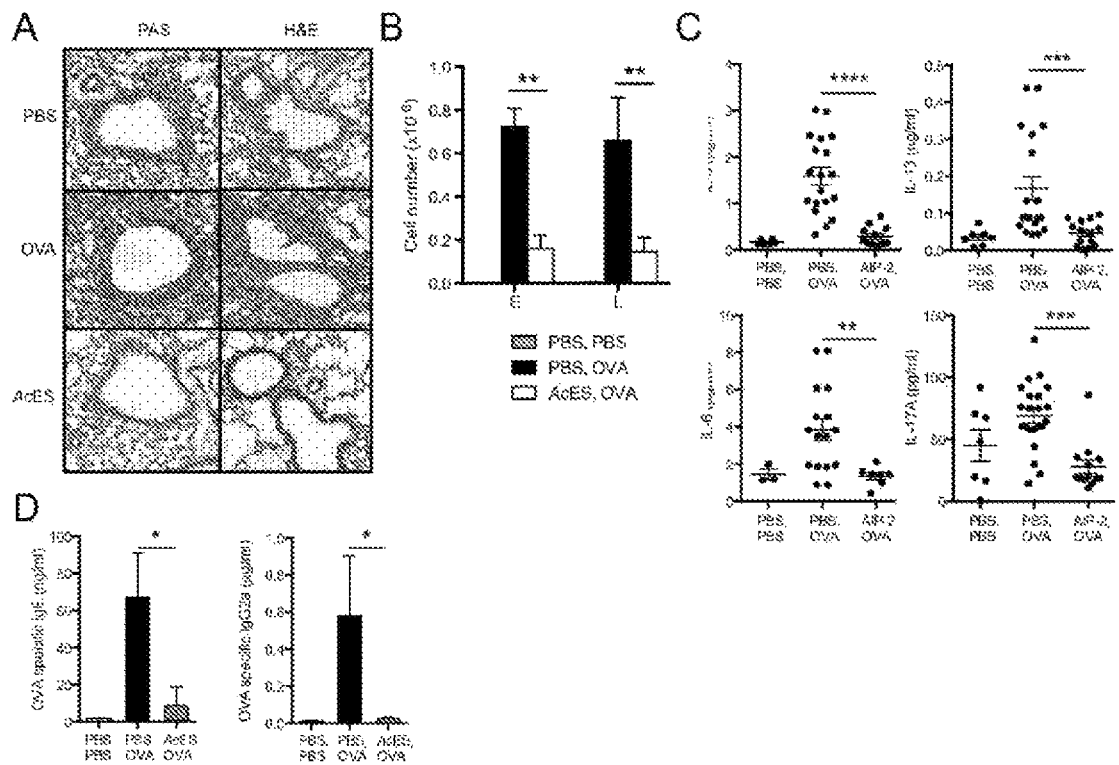
FIG. 9. *Ancylostoma caninum* excretory/secretory (ES) proteins suppress OVA-induced airway hyperresponsiveness, lung inflammation, mucus production and collagen deposition. (A) Lung sections were stained with haematoxylin and eosin (H&E) or Periodic acid Schiff (PAS). (B) Bronchoalveolar lavage cell analysis. (C) Concentrations of interleukin (IL)-5. IL-6, IL-13 and IL-17A in the lungs. (D) Levels of OVA-specific serum immunoglobulin (Ig)E and IgG2a. Results represent the mean of two independent experiments. *P≤0.05;  P≤0.01; * P≤0.001; **** P≤0.0001.

AcES-induced protection has been reported in models of Th1/17-mediated disease, typified by chemically induced colitis (15, 16), but not in primarily Th2-mediated models of inflammation, such as allergic airway disease. Here, we sensitized mice to OVA/Alum and treated with intra-peritoneal (i.p) AcES or vehicle (PBS). Compared to vehicle treated-mice, peribronchial and perivascular cellular infiltration of the lungs and mucus hypersecretion were significantly decreased in AcES-treated mice (FIG. 9a, b). Both lung Th2 cytokines, IL-5 and IL-13, and pro-inflammatory cytokines, IL-6 and IL-17A, were decreased following AcES treatment (FIG. 9c). Levels of IFN-γ were undetectable (data not shown). OVA-specific IgE and IgG2a serum titres were significantly decreased in AcES-treated mice compared to vehicle controls (FIG. 9d). Proteomics analysis of AcES (17) revealed abundant expression of two Tissue Inhibitor of Matrix Metalloprotease (TIMP)-like proteins, Ac-TMP-1 and TMP-2 (18, 19). In the absence of apparent metalloprotease-inhibitory properties for Ac-TMP-2 (20), and to avoid confusion around its proposed function, we have renamed it *Ancylostoma caninum* Anti-Inflammatory Protein-2 (Ac-AIP-2, or AIP-2) based on its anti-inflammatory properties described herein.

Figure 10:
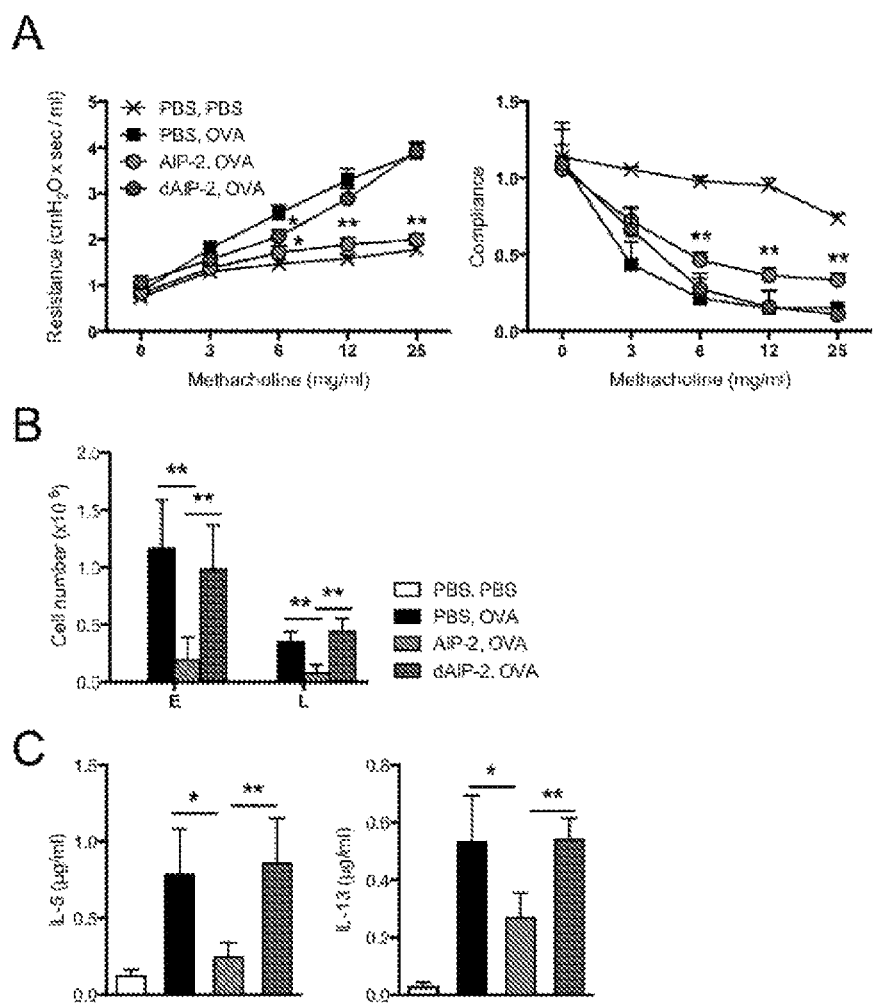
FIG. 10. Denaturation of Ac-AIP-2 (dAIP-2) restores OVA-induced airway inflammation. (A) Lung function assessed by invasive plethysmography measuring resistance and compliance in response to increasing doses of methacholine. (B) Frequencies of eosinophils (E) and lymphocytes (L) in the bronchoalveolar lavage fluid were assessed by flow cytometry. (C) Concentrations of interleukin-5 (IL-5), IL-6, IL-13 and IL-17A in the lungs. Results represent the mean of two independent experiments. *P≤0.05; ** P≤0.01.
Figure 11:
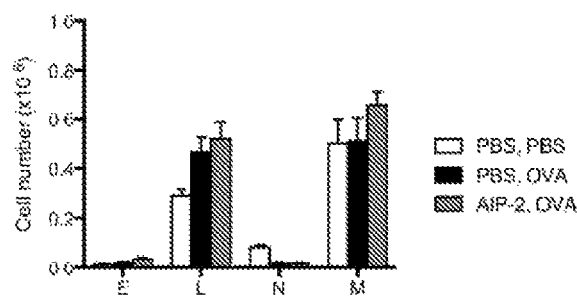
FIG. 11. Intraperitoneal administration of Ac-AIP-2 does not induce cellular infiltration at the site of injection. Differential cell count in the peritoneum of mice treated with AIP-2 or PBS and challenged with OVA or PBS. (E) eosinophils, (L) lymphocytes, (N) neutrophils, (M) macrophages. Results represent the mean of two independent experiments.
Figure 12:
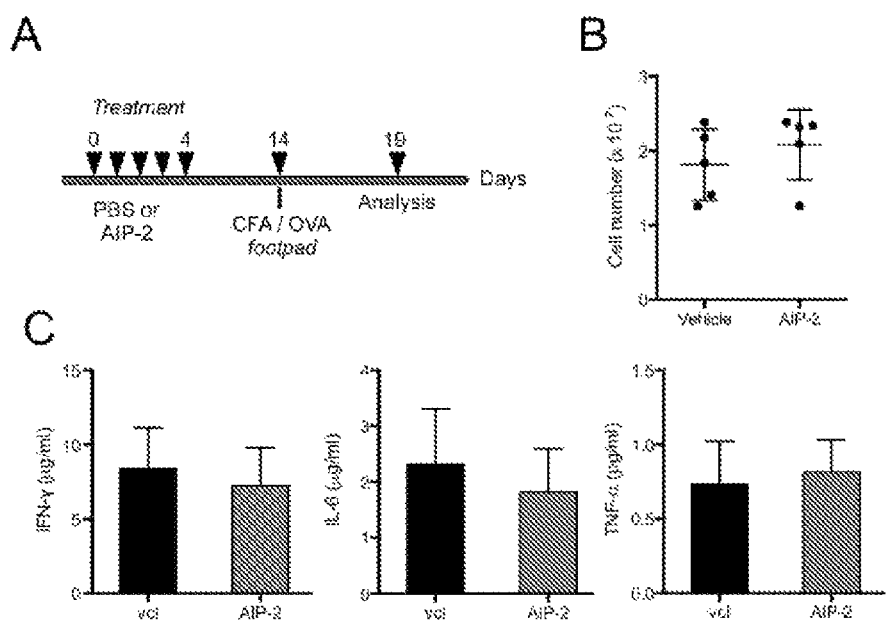
FIG. 12. Ac-AIP-2 does not protect against vaccination (adjuvanted)-induced Th1-type inflammation. (A) Schematic representation of the footpad administration of OVA in complete Freund's adjuvant in mice treated with AIP-2 intra-peritoneally. (B) Popliteal lymph node (PLN) cellularity. (C) 48-hour in vitro restimulation of PLN cells with anti-CD3 and anti-CD28 or OVA. Data show the concentration of IFN-γ, TNF-α and interleukin (IL)-6 collected in the supernatants and analysed by FACS array. Results represent the mean of two independent experiments.

In order to determine whether recombinant AIP-2 could protect against experimental asthma, mice were sensitized to OVA/alum, treated with AIP-2, heat/protease denatured AIP-2 (dAIP-2), or vehicle, and challenged with aerosolized OVA or PBS (FIGS. 5a, 10). Mice treated with AIP-2 displayed significant decreases in peribronchial and perivascular cellular infiltration of the lungs, mucus hypersecretion and collagen deposition (FIG. 5b). Lung resistance and compliance were significantly improved by AIP-2 treatment (FIG. 5c), and bronchoalveolar lavage fluid (BALF) differential cell count showed significant decreases in eosinophil and lymphocyte infiltrates in these mice (FIG. 5d). Mice treated with dAIP-2 were not protected against airway inflammation (FIG. 10a, b), and cytokine levels were significantly lower in the AIP-2 treated group compared to vehicle and dAIP-2 control groups (FIGS. 5e, 10c). Similarly. OVA-specific IgE and IgG2a serum titers were significantly lower in AIP-2 treated mice than controls (FIG. 5f). Injection (i.p.) of AcES leads to peritoneal eosinophilia (16). In order to verify that AIP-2 did not induce a similar effect, possibly explaining the absence of airway cellular infiltrate, peritoneal lavages from mice treated with AIP-2 were collected and found to contain the same numbers of eosinophils, lymphocytes, neutrophils and macrophages as controls (FIG. 11). To verify that AIP-2 did not have general immunosuppressive abilities, mice were treated with AIP-2 or vehicle then injected with OVA in complete Freund's adjuvant in the footpad. Popliteal lymph nodes were collected, cells counted and restimulated in vitro with OVA (FIG. 12a). Cellularity and levels of IFN-γ, IL-6, and TNF-α were similar in both AIP-2-treated and vehicle control mice (FIG. 12b, c).

Figure 13:
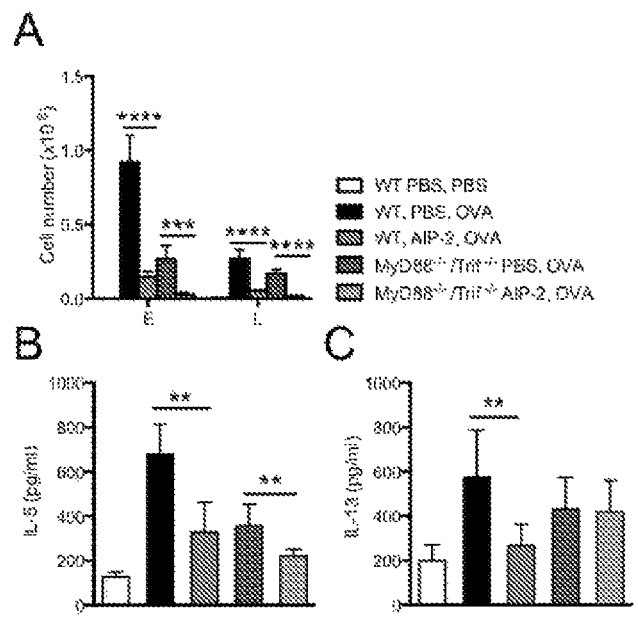
FIG. 13. Ac-AIP-2-induced protection does not require the activation of Toll-like receptors. (A) Bronchoalveolar lavage fluid analysis of WT or MyD88$^{-/-}$ Trif$^{-/-}$ mice treated with AIP-2 or not and challenged with OVA or PBS. (B-C) Concentrations of interleukin (IL)-5 and IL-13, respectively, in the lungs. Results represent the mean of two independent experiments.  P≤0.01; * P≤0.001; **** P≤0.0001.

In an attempt to understand the cellular mechanisms that govern AIP-2-mediated protection, we first wanted to identify whether toll-like receptor (TLR) signalling was involved. To this end, B6.MyD88$^{-/-}$/Trif$^{-/-}$ mice were sensitized to OVA and subsequently treated with AIP-2 or vehicle alongside wild-type (WT) mice. BALF differential cell count and lung IL-5 and IL-13 concentrations were not significantly different between WT and B6.MyD88$^{-/-}$/Trif$^{-/-}$ mice treated with AIP-2 or vehicle prior to challenge (FIG. 13).

Figure 6:
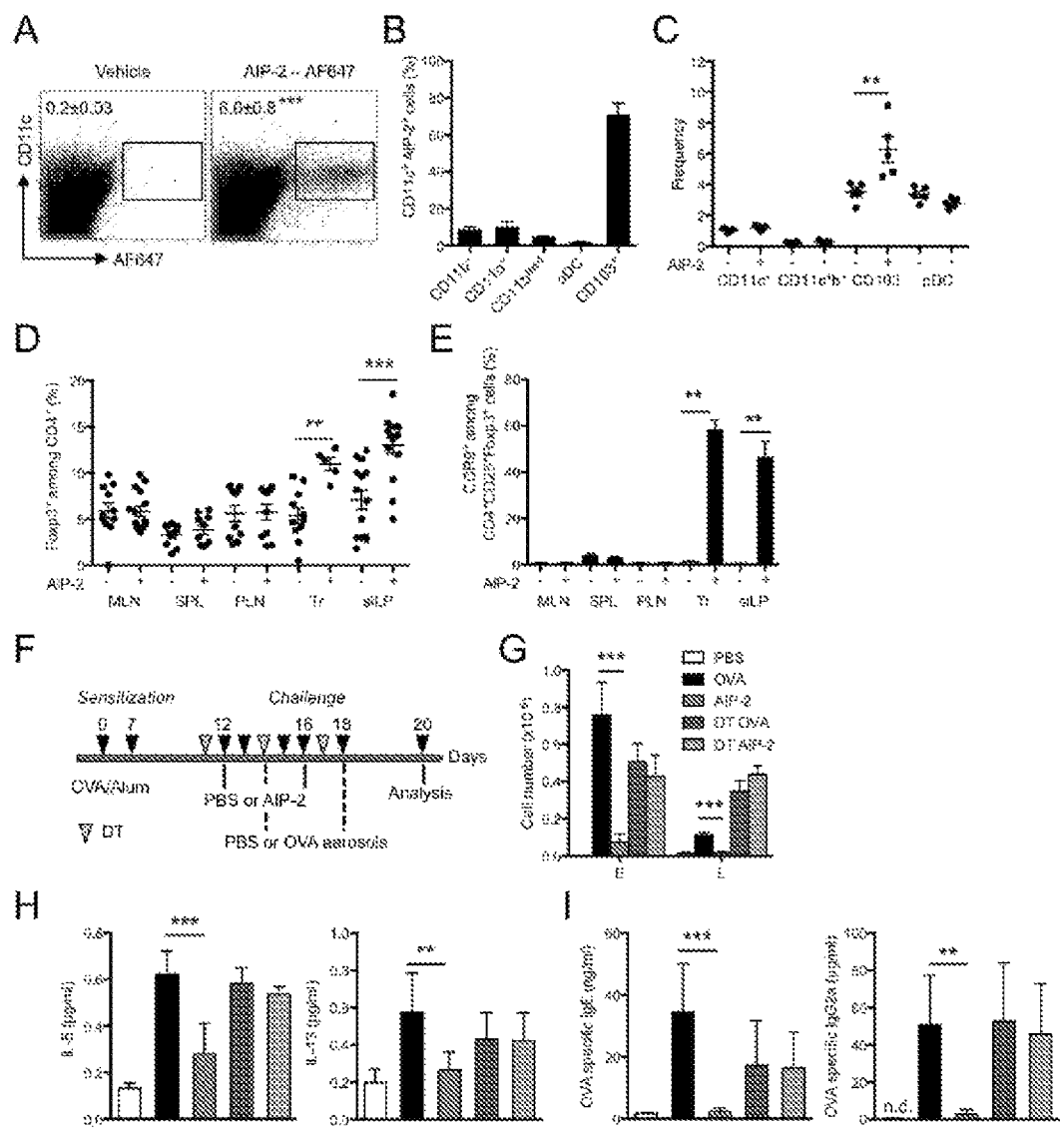
FIG. 6. AIP-2 is predominantly captured by $CD103^+$ dendritic cells (DC) and induces $CCR9^+$ regulatory T cells ($T_{reg}$) critical for the suppression of OVA-induced inflammation. (A-C) Mice were treated with Alexa Fluor (AF)-647 labelled Ac-AIP-2 or PBS for 5 days. (A) Frequency of AIP-2-AF-$647^+$ cells in the mesenteric lymph nodes (MLN). (B) Flow cytometry analysis of the $CD11c^+$ cells that captured AIP-2 in the MLN. (C) Expansion of the MLN DC subpopulations in mice treated with AIP-2 or vehicle. (D, E) Mice were treated with AIP-2 or vehicle daily for 5 days. Indicated tissues were collected, stained with anti-CD4, anti-CD25, anti-Foxp3 and anti-CCR9 mAbs and analysed by flow cytometry. (D) Frequency of $Foxp3^+$ cells among $CD3^+CD4^+$ T cells. (E) Frequency of CCR9 expressing cells among the $CD4^+CD25^+Foxp3^+$ $T_{reg}$ population. (F) Schematic representation of the experimental procedure with DEREG mice treated with diphtheria toxin (DT) or PBS. (G) Bronchoalveolar lavage fluid cell analysis by flow cytometry. (H) Concentration of interleukin (IL)-5 and IL-13 in the lungs. (I) Levels of OVA-specific immunoglobulin (Ig)E and IgG2a in the serum. Results represent the mean of three independent experiments. *P≤0.05;  P≤0.01; * P≤0.001.
Figure 14:
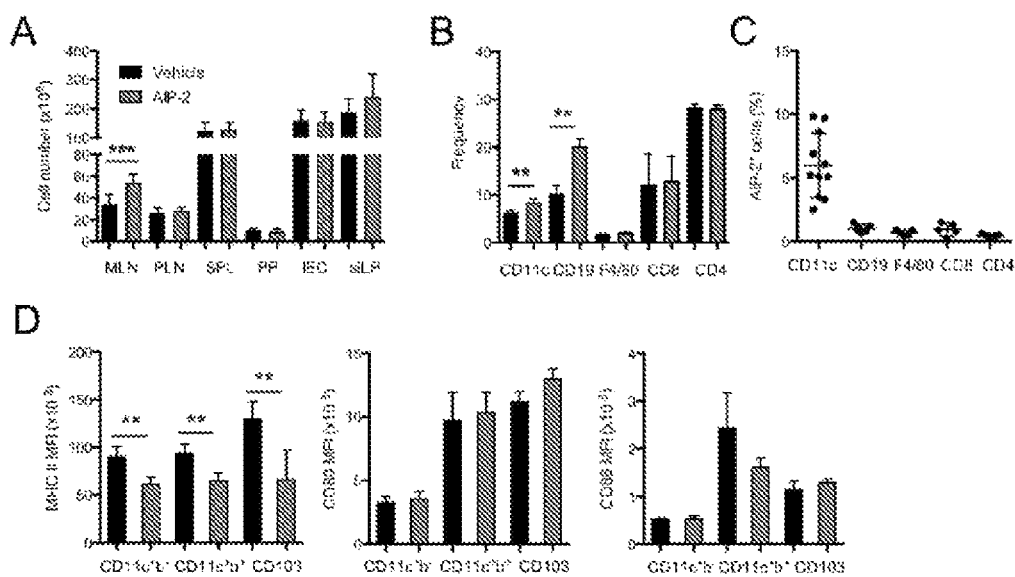
FIG. 14. Ac-AIP-2 treatment induces selective expansion of dendritic cells in the mesenteric lymph nodes (MLN). (A-C) Mice were treated with AIP-2 or vehicle daily for 5 days. (A) MLN cells were stained with surface markers and analysed for the expression of AIP-2-Alexa Fluor 647. (B) Indicated tissues were collected and counted. (C) MLN cells were stained with indicated surface markers and analysed by flow cytometry. (D) MLN of mice treated with AIP-2 conjugated to Alexa Fluor 647 or PBS were stained with surface and activation markers and analysed by flow cytometry. Results represent the mean of three independent experiments.  P≤0.01; * P≤0.001.

To further explore that cellular target of AIP-2, we sought to identify the specific tissue targeted by the treatment. Naïve mice were injected daily for 5 days with AIP-2 or vehicle. Multiple tissues were collected and analysed, revealing that mesenteric lymph node (MLN) cells were significantly expanded in relative comparison to the brachial, popliteal and inguinal lymph nodes, spleen, Peyer's patches, small intestine epithelial cells and lamina propria (FIG. 14a). To identify the cell populations in the MLN that associated with AIP-2 to mediate suppression of airway disease, AIP-2 was labelled with Alexa Fluor 647 and injected as above. While both the frequencies of CD11c$^+$ dendritic cells (DC) and CD19$^+$ B cells were significantly increased upon treatment (FIG. 14b), CD11c$^+$ cells were the main population to capture AIP-2 (FIGS. 6a, 14c). Further analysis demonstrated that the majority of AIP-2$^+$ CD11c$^+$ cells co-expressed CD103 (FIG. 6b), and this population was selectively expanded following AIP-2 treatment (FIG. 6c). While there was no difference in expression of CD80 and CD86 on all DC subpopulations analysed, AIP-2 administration induced a significant decrease in expression of MHCII (FIG. 14c), a finding in agreement with an earlier report on a different hookworm TIMP-like protein (21).

Both MLN CD103$^+$DCs and parasitic helminths are noted for their abilities to induce and maintain tolerance (22-24). Therefore, we examined the impact of AIP-2 treatment on CD4$^+$Foxp3$^+$ regulatory T cell (T$_{reg}$) populations. We observed a two-fold increase in T$_{reg}$ in the airway and intestinal mucosa upon treatment in comparison to vehicle (FIG. 6d), where T$_{reg}$ expressed the gut-homing receptor CCR9 (FIG. 6e). To assess the role of T$_{reg}$ in the protection induced by AIP-2 against airway inflammation, we utilized B6.Foxp3$^{DTR}$ (DEREG) mice. DEREG mice express a diphtheria toxin (DT) receptor-enhanced green fluorescent protein fusion protein under the control of the foxp3 gene locus, allowing selective and efficient depletion of Foxp3+ T$_{reg}$ (25). DEREG mice were sensitized to OVA, exposed to DT or not, treated with AIP-2 or vehicle, and challenged with aerosolized OVA or PBS (FIG. 6f). While a similar response to AIP-2 treatment was observed in DEREG mice that were not treated with DT, specific deletion of T$_{reg}$ completely abrogated the protection in these mice against eosinophilia and lymphocyte infiltration into the airways (FIG. 6g), production of IL-5 and IL-13 in the lungs (FIG. 6h), and OVA-specific serum IgE and IgG2a production (FIG. 6i).

Figure 7:
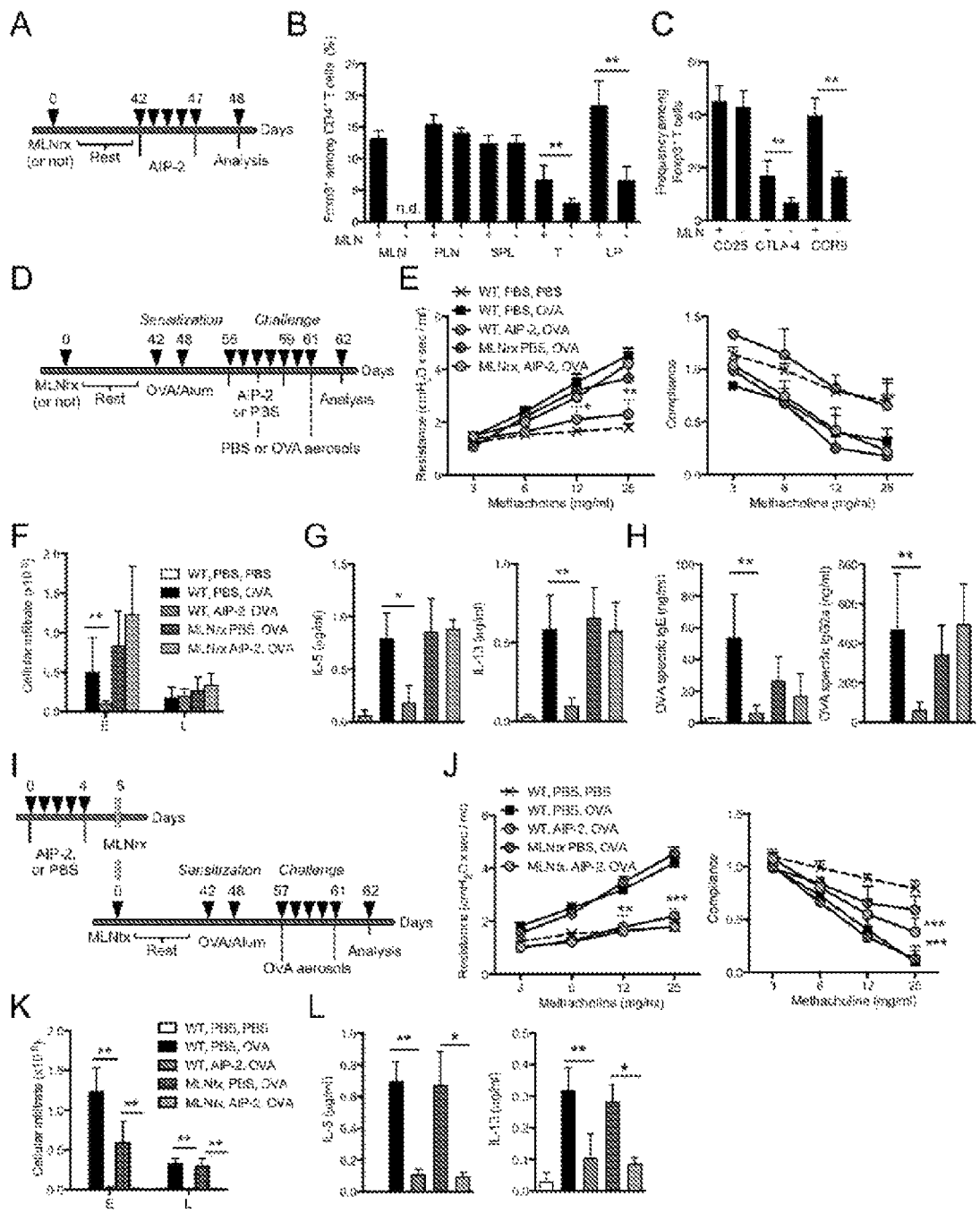
FIG. 7. Ac-AIP-2-induced regulatory T cells from the mesenteric lymph nodes (MLN) are critical for protection against OVA-induced lung inflammation. (A) Schematic representation of MLN resection experimental approach. (B, C) Indicated tissues were collected, stained with anti-CD4, anti-CD25, anti-Foxp3, anti-CTLA-4 and anti-CCR9 mAbs and analysed by flow cytometry. (D) Schematic representation of MLN-resected mice sensitised, treated or not with AIP-2, and challenged with OVA. (E) Resistance and compliance assessed by invasive plethysmography. (F) Frequencies of eosinophils (E) and lymphocytes (L) in the bronchoalveolar lavage fluid (BALF). (G) Concentrations of interleukin (IL)-5 and IL-13 in the lungs. (H) Levels of OVA-specific serum immunoglobulin (Ig)E and IgG2a. (I) Schematic representation of the MLN transplant (tx) experimental procedure. (3) Resistance and compliance in response to increasing doses of methacholine. (K) BALF analysis. (L) Concentration of IL-5 and IL-13 in the lungs. Results represent the mean of two independent experiments. *P≤0.05;  P≤0.01; * P≤0.001. n.d.—not detected.

MLN have specific properties that allow for the conversion of naïve T cells into T$_{reg}$ upon interaction with retinaldehyde dehydrogenase 2 and CD103$^+$ DCs, at which time they will be acquiring CCR9 (22, 26). To unequivocally demonstrate the origin of the immune response generated by AIP-2. MLN were surgically resected (rx), and mice were allowed to recover for 6 weeks (26), after which they were treated with AIP-2 (FIG. 7a). While no major difference in the frequency of CD4$^+$ Foxp3$^+$ cells was observed in the periphery between WT and MLNrx mice, T$_{reg}$ were significantly decreased in airway and intestinal mucosa of MLNrx mice (FIG. 7b). A significant decrease in CCR9- and CTLA-4-expressing T$_{reg}$ in the small intestine lamina propria supports the evidence that AIP-2 induces de novo T$_{reg}$ that originate from the mesenteries (FIG. 7c). To validate the critical role of the mesenteries in the protection against airway inflammation, mice underwent MLNrx or not, were subsequently sensitized to OVA, treated with AIP-2 or vehicle, and challenged with OVA or PBS aerosols once the recovery period was complete (FIG. 7d). MLNrx mice treated with AIP-2 were not protected against airway hyper-responsiveness, airway infiltration of eosinophils, lung production of IL-5 and IL-13, and OVA-specific serum IgE and IgG2a (FIG. 7e-h). Finally, to examine whether AIP-2 modifies the MLN microenvironment, mice were treated with AIP-2 or vehicle as previously described, and MLN were surgically removed and transplanted into naïve recipients in replacement of the host's mesenteric tissue (FIG. 7i). After recovery, mice were sensitized to OVA and challenged with OVA or PBS aerosols. Nine weeks after the transplant, mice that received MLNtx from AIP-2-treated donors were still protected against airway hyperresponsiveness, lung eosinophilia, BALF lymphocyte infiltration, and lung IL-5 and IL-13 production (FIG. 7j-l).

Figure 8:
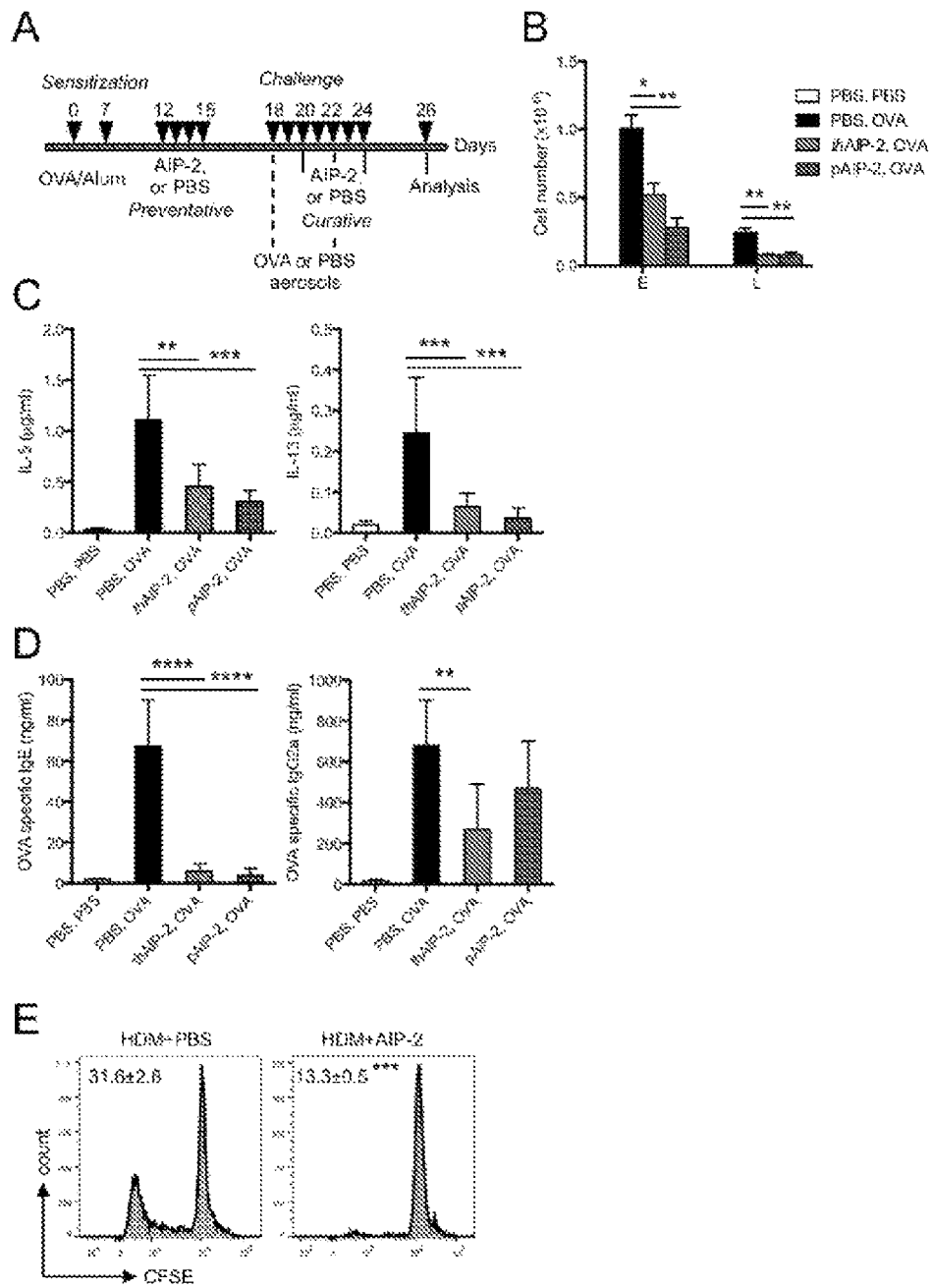
FIG. 8. Therapeutic or preventative mucosal delivery of Ac-AIP-2 protects against allergic inflammation in mice and suppresses ex vivo house dust mite-specific T cell proliferation in humans. (A) Schematic representation of the intranasal administration of AIP-2 as a preventative (p) or therapeutic (th) approach in experimental murine asthma. (B) Bronchoalveolar lavage fluid analysis. (C) Concentration of interleukin (IL)-5 and IL-13 in the lungs. (D) Levels of OVA-specific serum immunoglobulin (Ig)E and IgG2a. (e) Whole blood from House Dust Mite (HDM) sensitised patients was prepared and stained with CFSE. Cells were incubated with HDM extract in the presence of AIP-2 or vehicle for 5 days. Cells were stained with human anti-CD3 and anti-CD4, and analysed for CFSE dilutions by flow cytometry. Results represent the mean of three independent experiments. *P≤0.05;  P≤0.01; * P≤0.001; **** P≤0.0001.

Administration of human biologics is typically via the parenteral route, but less invasive delivery systems are desirable (27). To determine whether AIP-2 could prevent airway inflammation when delivered directly to the mucosa, we administered it intra-nasally as a bolus into the lungs (FIG. 8a), whereupon it induced significant protection against eosinophil recruitment to and Th2 cytokine production in the lungs (FIG. 8b, c), as well as significant reductions in OVA-specific serum IgE and IgG2a titers (FIG. 8d). Moreover, to determine whether AIP-2 could suppress OVA-induced airway inflammation once it is already established, mice were injected with AIP-2 daily for 4 days commencing two days after the first OVA aerosol administration (FIG. 8a). Therapeutic delivery of AIP-2 during aerosol challenges induced significant protection against eosinophil recruitment to and Th2 cytokine production in the lungs, and OVA-specific serum IgE (FIG. 8b-d).

Finally, to determine whether AIP-2 had immunoregulatory properties that acted upon human cells, PBMCs were isolated from human subjects with clinically characterized house dust mite (HDM) allergy. Cells were labelled with CFSE and stimulated with HDM extract in the presence of AIP-2 or vehicle for 5 days. HDM stimulation of PBMCs resulted in a specific proliferative response that was significantly reduced in the presence of AIP-2 (FIG. 8e).

In summary. AIP-2 offers potent protection against allergic airway inflammation via a novel mechanism of action involving the activation and expansion of $T_{reg}$ by CD103$^+$ DCs in the MLN. AIP-2-induced $T_{reg}$ likely undergo extrathymic differentiation, and might therefore control mucosal Th2 inflammation via direct effects on the composition of commensal microbial communities in the lung or the gut (28, 29). The mechanism of action for AIP-2 is different to that of other helminth recombinant proteins that suppress inflammation, typically via IL-10-producing type 2 macrophages or modulation of voltage-gated potassium channels on memory T cells (13, 14, 30). Our findings show an important and long-lasting effect of AIP-2, promoting the generation of regulatory responses without inducing general immunosuppression. AIP-2 seems to reset the balance of effector to regulatory T cell responses by generating a long-term imprint on lymphoid tissues, a phenomenon that has not been previously reported for a purified protein. Our study highlights the therapeutic potential of helminth recombinant proteins, a more palatable and easily regulated therapeutic modality than experimental helminth infection. This novel class of biologics has appeal for a broad range of inflammatory diseases that have reached alarming prevalence in industrialized nations.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. P. J. Cooper, M. E. Chico, L C. Rodrigues, M. Ordonez, D. Strachan, G. E. Griffin. T. B. Nutman, Reduced risk of atopy among school-age children infected with geohelminth parasites in a rural area of the tropics. *J. Allergy Clin. Immunol.* 111, 995-1000 (2003).
2. A. M. Croft, P. Bager, S. Kumar. Helminth therapy (worms) for allergic rhinitis. *Cochrane Database Syst. Rev.* 4, CD009238 (2012).
3. L. J. Wammes, H. Mpairwe, A. M. Elliott, M. Yazdanbakhsh, Helminth therapy or elimination: epidemiological, immunological, and clinical considerations. *Lancet Infect. Dis.* (2014).
4. S. Scrivener, H. Yemaneberhan, M. Zebenigus, D. Tilahun, S. Girma, S. Ali, P. McElroy, A. Custovic, A. Woodcock, D. Pritchard, A. Venn, J. Britton, Independent effects of intestinal parasite infection and domestic allergen exposure on risk of wheeze in Ethiopia: a nested case-control study. *Lancet* 358, 1493-1499 (2001).
5. M. J. Broadhurst, J. M. Leung, V. Kashyap, J. M. McCune, U. Mahadevan, J. H. McKerrow, P. Loke, IL-22+ CD4+ T cells are associated with therapeutic Trichuris trichiura infection in an ulcerative colitis patient. *Sci. Transl. Med.* 2, 60ra88 (2010).
6. J. Croese, J. O'Neil, J. Masson, S. Cooke, W. Melrose, D. Pritchard, R. Speare, A proof of concept study establishing Necator americanus in Crohn's patients and reservoir donors. *Gut* 55, 136-137 (2006).
7. R. W. Summers, D. E. Elliott, J. F. Urban, Jr., R. A. Thompson, J. V. Weinstock, Trichuris suis therapy for active ulcerative colitis: a randomized controlled trial. *Gastroenterology* 128, 825-832 (2005).
8. J. O. Fleming. Helminths and multiple sclerosis: will old friends give us new treatments for MS?*J. Neuroimmunol.* 233, 3-5 (2011).
9. J. R. Feary, A. J. Venn, K. Mortimer, A. P. Brown, D. Hooi, F. H. Falcone, D. I. Pritchard, J. R. Britton, Experimental hookworm infection: a randomized placebo-controlled trial in asthma. *Clin. Exp. Allergy* 40, 299-306 (2010).
10. J. Croese. S. Navarro, A. Clouston, L McCann, A. Dougall, I. Ferreira, A. Susianto, P. O'Rourke, M. Howlett, J. McCarthy, C. Engwerda, D. Jones, A. Loukas A, Experimental hookworm infection and gluten micro-challenge promotes tolerance in celiac disease. *J. Allergy Clin. Immunol.* in press, (2014).
11. D. E. Elliott, J. V. Weinstock, Helminth-host immunological interactions: prevention and control of immune-mediated diseases. *Ann. N. Y. Acad. Sci.* 1247, 83-96 (2012).
12. P. Adisakwattana, S. P. Saunders, H. J. Nel, P. G. Fallon, Helminth-derived immunomodulatory molecules. *Adv. Exp. Med. Biol.* 666, 95-107 (2009).
13. C. Schnoeller, S. Rausch, S. Pillai, A. Avagyan, B. M. Wittig, C. Loddenkemper, A. Hamann, E. Hamelmann, R. Lucius, S. Hartmann, A helminth immunomodulator reduces allergic and inflammatory responses by induction of IL-10-producing macrophages. *J. Immunol.* 180, 4265-4272 (2008).
14. S. Chhabra, S. C. Chang, H. M. Nguyen, R. Huq, M. R. Tanner, L. M. Londono, R. Estrada, V. Dhawan, S. Chauhan, S. K. Upadhyay, M. Gindin, P. J. Hotez, J. G.

Valenzuela, B. Mohanty, J. D. Swarbrick, H. Wulff, S. P. Iadonato, G. A. Gulman, C. Beeton, M. W. Pennington, R. S. Norton. K. G. Chandy, Kv1.3 channel-blocking immunomodulatory peptides from parasitic worms: implications for autoimmune diseases. *FASEB J.* (2014).
15. N. E. Ruyssers, B. Y. De Winter, J. G. De Man, A. Loukas, M. S. Pearson, J. V. Weinstock. R. M. Van den Bossche, W. Martinet, P. A. Pelckmans, T. G. Morcels, Therapeutic potential of helminth soluble proteins in TNBS-induced colitis in mice. *Inflamm. Bowel Dis.* 15, 491-500 (2009).
16. I. Ferreira, D. Smyth, S. Gaze, A. Aziz. P. Giacomin, N. Ruyssers, D. Artis, T. Laha, S. Navarro, A. Loukas, H. J. McSorley, Hookworm excretory/secretory products induce interleukin-4 (IL-4)+ IL-10+ CD4+ T cell responses and suppress pathology in a mouse model of colitis. *Infect. Immun.* 81, 2104-2111 (2013).
17. J. Mulvenna, B. Hamilton, S. H. Nagaraj, D. Smyth, A. Loukas, J. J. Gorman, Proteomics analysis of the excretory/secretory component of the blood-feeding stage of the hookworm, *Anclostoma caninum. Mol. Cell. Proteomics* 8, 109-121 (2009).
18. B. Zhan, R. Gupta, S. P. Wong, S. Bier. D. Jiang, G. Goud, P. Hotez, Molecular cloning and characterization of Ac-TMP-2, a tissue inhibitor of metalloproteinase secreted by adult *Ancylosloma caninum. Mol. Biochem. Parasitol.* 162, 142-148 (2008).
19. B. Zhan, M. Badamchian, B. Meihua, J. Ashcom, J. Feng, J. Hawdon, X. Shuhua, P. J. Hotez, Molecular cloning and purification of Ac-TMP, a developmentally regulated putative tissue inhibitor of metalloprotease released in relative abundance by adult *Ancylostoma* hookworms. *Am. J. Trop. Med. Hyg.* 66, 238-244 (2002).
20. C. Cantacessi. A. Hofmann, D. Pickering, S. Navarro, M. Mitreva, A. Loukas, TIMPs of parasitic helminths—a large-scale analysis of high-throughput sequence datasets. *Parasit. Vectors* 6, 156 (2013).
21. C. Cuellar, W. Wu, S. Mendez, The hookworm tissue inhibitor of metalloproteases (Ac-TMP-1) modifies dendritic cell function and induces generation of CD4 and CD8 suppressor T cells. *PLoS Negl. Trop. Dis.* 3, e439 (2009).
22. J. L. Coombes, K. R. Siddiqui, C. V. Arancibia-Carcamo, J. Hall, C. M. Sun, Y. Belkaid, F. Powrie, A functionally specialized population of mucosal CD103+ DCs induces Foxp3+ regulatory T cells via a TGF-beta and retinoic acid-dependent mechanism, *J. Exp. Med.* 204, 1757-1764 (2007).
23. U. G. Strauch, N. Grunwald, F. Obermeier, S. Gurster, H. C. Rath, Loss of CD103+ intestinal dendritic cells during colonic inflammation, *World J. Gastroenterol.* 16, 21-29 (2010).
24. J. E. Allen, R. M. Maizels, Diversity and dialogue in immunity to helminths. *Nat. Rev. Immunol.* 11, 375-388 (2011).
25. K. Lahl, C. Loddenkemper, C. Drouin, J. Freyer, J. Arnason, G. Eberl, A. Hamann, H. Wagner, J. Huehn, T. Sparwasser, Selective depletion of Foxp3+ regulatory T cells induces a scurfy-like disease. *J. Exp. Med.* 204, 57-63 (2007).
26. M. Ahrendt, S. I. Hammerschmidt, O. Pabst, R. Pabst, U. Bode, Stromal cells confer lymph node-specific properties by shaping a unique microenvironment influencing local immune responses. *J. Immunol.* 181, 1898-1907 (2008).
27. N. Skalko-Basnet, Biologics: the role of delivery systems in improved therapy. *Biol. Targets Ther.* 8, 107-114 (2014).
28. S. Z. Josefowicz, R. E. Niec, H. Y. Kim, P. Treuting, T. Chinen, Y. Zheng. D. T. Umetsu, A. Y. Rudensky, Extrathymically generated regulatory T cells control mucosal TH2 inflammation. *Nature* 482, 395-399 (2012).
29. E. S. Gollwitzer, S. Saglani, A. Trompette, K. Yadava, R. Sherburn, K. D. McCoy, L. P. Nicod, C. M. Lloyd, B. J. Marsland, Lung microbiota promotes tolerance to allergens in neonates via PD-L1. *Nat. Med.* 20, 642-647 (2014).
30. M. W. Robinson, R. Alvarado, J. To, A. T. Hutchinson, S. N. Dowdell, M. Lund, L. Turnbull, C. B. Whitchurch, B. A. O'Brien, J. P. Dalton, S. Donnelly, A helminth cathelicidin-like protein suppresses antigen processing and presentation in macrophages via inhibition of lysosomal vATPase. *FASEB J.* 26, 4614-4627 (2012).
31. N. Ranjit, B. Zhan, D. J. Stenzel, J. Mulvenna, R. Fujiwara. P. J. Hotez, A. Loukas, A family of cathepsin B cysteine proteases expressed in the gut of the human hookworm, *Necator americanus. Mol. Biochem. Parasitol.* 160, 90-99 (2008).
32. S. Navarro, G. Cossalter, C. Chiavaroli, A. Kanda, S. Fleury, A. Lazzari, J. Cazareth, T. Sparwasser, D. Dombrowicz, N. Glaichenhaus, V. Julia, The oral administration of bacterial extracts prevents asthma via the recruitment of regulatory T cells to the airways. *Mucosal Immunol.* 4, 53-65 (2011).
33. B. Weigmann, I. Tubbe, D. Seidel, A. Nicolaev, C. Becker, M. F. Neurath, Isolation and subsequent analysis of murine lamina propria mononuclear cells from colonic tissue. *Nat. Protocols* 2, 2307-2311 (2007).

The invention claimed is:

1. A method for reducing or alleviating inflammation in a subject, the method including the step of administering to the subject a therapeutically effective amount of a modified Ac-TMP-2 protein, wherein the modified Ac-TMP-2 protein consists of:

an amino acid sequence set forth in SEQ ID NO:1 or SEQ ID NO:5, or an amino acid sequence at least 95% identical thereto;

optionally, a heterologous signal peptide amino acid sequence;

optionally, a heterologous C-terminal amino acid sequence;

wherein the modified Ac-TMP-2 protein is capable of preventing, reducing and/or alleviating inflammation upon administration to a subject, to thereby reduce or alleviate the inflammation.

2. The method of claim 1, wherein the inflammation is associated with, or secondary to, a disease, disorder and/or condition in the subject.

3. The method of claim 2, wherein the disease, disorder and/or condition is refractory to a baseline therapy.

4. The method of claim 2, wherein the disease, disorder and/or condition is an immunological disease, disorder and/or condition.

5. The method of claim 2, wherein the disease is a disease of the digestive tract.

6. The method of claim 5, wherein the disease is chronic gastritis or a inflammatory bowel disease.

7. The method of claim 6, wherein the inflammatory bowel disease is Crohn's disease or ulcerative colitis.

8. The method of claim 2, wherein the disease is a disease of the respiratory system.

9. The method of claim 8, wherein the disease is selected from the group consisting of asthma, emphysema, chronic bronchitis, and chronic obstructive pulmonary disease (COPD).

10. The method of claim 1, further including the step of administering to the subject at least one additional agent.

11. The method of claim 10, wherein the at least one additional agent is selected from the group consisting of nonsteroidal anti-inflammatory drugs (NSAIDs), aminosalicylates, corticosteroids, immunosuppressants, anti-cytokine/cytokine receptor agents, antibiotics, and combinations thereof.

* * * * *